(12) United States Patent
Hada et al.

(10) Patent No.: US 6,870,142 B2
(45) Date of Patent: Mar. 22, 2005

(54) POWER SUPPLY CONTROL SYSTEM FOR HEATER USED IN GAS SENSOR

(75) Inventors: Satoshi Hada, Inazawa (JP); Eiichi Kurokawa, Okazaki (JP); Mitsunobu Niwa, Kariya (JP)

(73) Assignee: Denso Corporation, Kariya (JP)

( * ) Notice: Subject to any disclaimer, the term of this patent is extended or adjusted under 35 U.S.C. 154(b) by 474 days.

(21) Appl. No.: 10/157,866

(22) Filed: May 31, 2002

(65) Prior Publication Data

US 2002/0179443 A1 Dec. 5, 2002

(30) Foreign Application Priority Data

May 31, 2001 (JP) ........................................ 2001-164599
Apr. 9, 2002 (JP) ........................................ 2002-106331

(51) Int. Cl.[7] ................................................ H05B 1/02
(52) U.S. Cl. ........................................ 219/494; 219/497
(58) Field of Search .................................. 219/202, 205, 219/482, 490, 492, 494, 497, 504, 509, 510; 123/681, 687, 688, 690, 697; 204/401, 425, 426, 427, 406, 408

(56) References Cited

U.S. PATENT DOCUMENTS 6,009,866 A * 1/2000 Sagisaka et al. ............ 123/681
6,083,370 A 7/2000 Kato et al.
6,540,892 B1 * 4/2003 Strohmaier ................. 204/408
6,651,639 B2 * 11/2003 Hada et al. ................. 123/697
6,812,436 B2 * 11/2004 Nomura et al. ............. 219/497

FOREIGN PATENT DOCUMENTS

JP        10-232220        9/1998
JP        10-300716        11/1998
JP        2000-65780       3/2000

* cited by examiner

Primary Examiner—Tu Hoang
(74) Attorney, Agent, or Firm—Nixon & Vanderhye P.C.

(57) ABSTRACT

A heater control system is provided for controlling the temperature of a heater used to heat a solid electrolyte-made sensor element of a gas concentration sensor up to a given temperature at which the sensor element is activated to provide a correct gas concentration output for controlling a preselected variable used in, for example, an automotive air-fuel ratio control system. The heater control system measures a resistance value of the sensor element and controls an electric power supplied to the heater as a function of the resistance value. The heater control system is designed to determine a controlled variable properly used to control the heater, thereby resulting in improved controllability of a power supply to the heater and also works to minimize an error in determining the resistance of the heater.

22 Claims, 14 Drawing Sheets sor element of a gas concentration sensor up to a temperature at which the sensor element is activated to provide a correct gas concentration output. The heater control apparatus comprises: (a) a control circuit working to control a power supply to the heater; (b) a sensor element resistance determining circuit working to determine a resistance value of the sensor element of the gas concentration sensor; (c) a heater control variable determining circuit determining a heater control variable for controlling the power supply to the heater in the control circuit as a function of a difference between the resistance value determined by the sensor element resistance determining circuit and a target value; and (d) a heater control variable correcting circuit correcting the heater control variable determined by the heater control variable determining circuit based on a comparison between a given reference heater power and a heater power actually used in the heater. Even if the voltage of a power source for the heater is changed or the voltage applied to the heater through a harness is changed, thereby resulting in a change in power supplied to the heater, it is possible to determine the heater control variable correctly. This results in improved controllability of the heater. The resistance value of the sensor element may be the impedance or admittance of the sensor element.

POWER SUPPLY CONTROL SYSTEM FOR HEATER USED IN GAS SENSOR

BACKGROUND OF THE INVENTION

1. Technical Field of the Invention

The present invention relates generally to a power supply control system for a heater working to heat a gas sensor such as a gas concentration sensor up to a desired activation temperature which may be employed in an air-fuel ratio control system for automotive vehicles for measuring the concentration of a specified component such as $O_2$, NOx, or CO contained in exhaust emissions from the engine.

2. Background Art

Air-fuel ratio control for automotive internal combustion engines is typically accomplished using an output of a gas concentration sensor. Such a gas concentration sensor has a sensor element which includes a solid electrolyte member made of zirconia. The sensor element works to measure the concentration of a given gas component (e.g., oxygen) of exhaust gasses of the engine. An air-fuel ratio control system determines an air-fuel ratio as a function of the measured concentration of the gas component. Ensuring the accuracy of such a determination requires keeping the sensor element at a desired activation temperature. This is usually achieved using a heater embedded in the sensor element. The amount of heat generated by the heater is regulated, for example, by changing the duty cycle of a pulse signal used to switching on and off a power supply to the heater. A feedback control system is proposed which measures the resistance of the sensor element and achieves the regulation of the power supply by changing the duty cycle of the pulse signal to bring the measured resistance to agreement with a target one.

The gas concentration sensor usually undergoes an undesirable change in power supply due to a drop in voltage applied to the heater through a harness and/or a change in output voltage of a power source. This results in lowered controllability of the power supply to the heater.

Further, switching between on-time and off-time of the duty cycle of the pulse signal usually cause electric noises to be added to the harness coupled to the heater. Therefore, if such switching overlaps with a period of time during which the resistance of the sensor element is measured, it may result in an error in measuring the resistance of the sensor element. This problem is encountered frequently, especially in a case where harnesses leading to the sensor element and to the heater are tied together.

SUMMARY OF THE INVENTION

It is therefore a principal object of the present invention to avoid the disadvantages of the prior art.

It is another object of the present invention to provide a heater control system for gas concentration sensors which is designed to determine a controlled variable properly used to control a heater built in the gas concentration sensor, thereby resulting in improved controllability of a power supply to the heater.

It is a further object of the invention to provide a heater control system for gas concentration sensors which works to minimize an error in determining the resistance of a heater built in the gas concentration sensor.

According to one aspect of the invention, there is provided a heater control apparatus for controlling a temperature of a heater used to heat a solid electrolyte-made sensor In the preferred mode of the invention, the heater control variable correcting circuit corrects the heater control variable based on a comparison between a voltage appearing at the heater and a reference voltage preselected for the heater.

The heater control variable correcting circuit may alternatively correct the heater control variable based on a comparison between a current flowing through the heater and a reference current preselected for the heater.

A guard value providing means is further provided for providing a guard value working to defines a limit of the heater control variable. The guard value may be increased with an increase in the resistance value of the sensor element determined by the sensor element resistance determining circuit.

The control circuit works to supply power to the heater in a cycle and controls an on-time for which the power is supplied to the heater. The control circuit allows the heater control variable correcting circuit to determine one of a heater voltage developed at the heater and a current flowing through the heater which is employed to determine the heater power consumed in the heater only when the on-time is longer than a given reference value.

The control circuit is responsive to the heater control variable to switch the power supply to the heater on and off cyclically. The sensor element resistance determining circuit measures the resistance value of the sensor element in a cycle by changing one of a voltage applied to the heater and a current flowing through the heater instantaneously, monitoring a change in the one of the voltage and the current, and calculating the resistance value as a function of the change. When it is determined that an on-off switching time at which the power supply to the heater is to be switched on or off will overlap with a measurement time for which the resistance value is to be measured, the sensor element resistance determining circuit shifts one of the on-off switching time and the measurement time.

According to the second aspect of the invention, there is provided a heater control apparatus which comprises: (a) a control circuit controlling a power supply to a heater used to heat a solid electrolyte-made sensor element of a gas concentration sensor up to a temperature at which the sensor element is activated to provide a desired gas concentration output; (b) a sensor element resistance determining circuit working to determine a resistance value of the sensor element of the gas concentration sensor; (c) a heater control variable determining circuit determining a heater control variable which is used in the control circuit in controlling the power supply to the heater as a function of a difference between the resistance value determined by the sensor element resistance determining circuit and a target value; and (d) a heater control variable correcting circuit determining one of a heater voltage developed at the heater and a heater current flowing through the heater in a cycle. The heater control variable correcting circuit corrects the heater control variable determined by the heater control variable determining circuit based on a comparison between one of the heater voltage and the heater current as determined in a current cycle and a corresponding one of the heater voltage and the heater current as determined in a previous cycle. Even if the voltage of a power source for the heater is changed or the voltage applied to the heater through a harness is changed, thereby resulting in a change in power supplied to the heater, it is possible to determine the heater control variable correctly. This results in improved controllability of the heater. The resistance value of the sensor element may be the impedance or admittance of the sensor element.

In the preferred mode of the invention, the apparatus also includes a guard value providing means for providing a guard value which works to define a limit of the heater control variable. The guard value is increased with an increase in the resistance value of the sensor element determined by the sensor element resistance determining circuit.

The control circuit provides a power supply control signal to a heater driver to bring the resistance value into agreement with the target value under feedback control for controlling the power supply to the heater. The power supply control signal is provided using a mathematical formula including an integral term in terms of the difference between the resistance value determined by the sensor element resistance determining circuit and the target value. The apparatus also includes a decision means for deciding whether the resistance value as determined by the sensor element resistance determining circuit falls within a given controlled range or not. When it is determined by the decision means that the resistance value lies out of the given range, the guard value providing means determines the guard value so as to decrease a change in the resistance value from the target value.

The guard value providing means defines a first guard value and a second guard value. The first guard value is provided to determine a maximum value of the heater control variable when the decision means determines that the resistance value lies out of the given controlled range to a side on which a temperature of the sensor element is higher. The second guard value is provided to determine a minimum value of the heater control variable when the decision means that the resistance value lies out of the given controlled range to a side on which the temperature of the sensor element is lower.

The control circuit works to supply power to the heater in a cycle and controls an on-time for which the power is supplied to the heater. The control circuit allows the heater control variable correcting circuit to determine one of a heater voltage developed at the heater and a current flowing through the heater which is employed to determine the heater power consumed in the heater only when the on-time is longer than a given reference value.

The control circuit is responsive to the heater control variable to switch the power supply to the heater on and off cyclically. The sensor element resistance determining circuit measures the resistance value of the sensor element in a cycle by changing one of a voltage applied to the heater and a current flowing through the heater instantaneously, monitoring a change in the one of the voltage and the current, and calculating the resistance value as a function of the change. When it is determined that an on-off switching time at which the power supply to the heater is to be switched on or off will overlap with a measurement time for which the resistance value is to be measured, one of the on-off switching time and the measurement time is shifted.

According to the third aspect of the invention, there is provided a gas concentration sensor control apparatus comprising: (a) a gas concentration sensor having a solid electrolyte-made sensor element producing a sensor output indicative of a concentration of a specified gas component: (b) a heater installed in the gas concentration sensor to heat the sensor element up to a temperature at which the sensor element is activated to produce the sensor output correctly; (c) a heater power supply control circuit working to turn on and off a power supply to the heater cyclically; (d) a sensor element resistance determining circuit working to measure a resistance value of the sensor element in a cycle by changing one of a voltage applied to the heater and a current flowing through the heater instantaneously, monitoring a change in the one of the voltage and the current, and calculating the resistance value as a function of the change; (e) a heater control variable determining circuit determining a heater control variable, which is used in the heater power supply control circuit to define an on-time for which the power supply to the heater is to be turned on and an off-time for which the power supply to the heater is to be turned off, as a function of a difference between the resistance value determined by the sensor element resistance determining circuit and a target value; and (f) a control circuit determining whether an on-off switching time at which the power supply to the heater is to be switched on or off will overlap with a measurement time for which the resistance value is to be measured. When it is determined that the on-off switching time will overlap with the measurement time, the control circuit shifts one of the on-off switching time and the measurement time. This enables the resistance value to be determined correctly without addition of an electric noise arising from the on-off switching of the power supply to the heater.

In the preferred mode of the invention, when it is determined that the on-off switching time will overlap with the measurement time, the control circuit brings the on-off switching time outside the measurement time.

When it is determined that the on-off switching time will overlap with the measurement time, the control circuit brings the on-off switching time outside one of start and end of the measurement time which results in a smaller change in either of the on-time and the off-time.

When it is determined that the on-off switching time will overlap with the measurement time, the control circuit may alternatively delay measurement of the resistance value until completion of on-off switching of the power supply to the heater.

The heater control variable is a duty cycle of a power supply control signal that is a ratio of the on-time to the off-time. When it is determined that the on-off switching time will overlap with the measurement time, the control circuit increases or decreases the duty cycle.

The duty cycle may be synchronized with the measurement time. An upper or a lower value of the duty cycle is determined to prevent the on-off switching time from overlapping with the measurement time.

The gas concentration sensor may have a plurality of cells disposed on a solid electrolyte body of the sensor element. The sensor element resistance determining circuit measures respective resistance values of the cells to determine the resistance value of the sensor element. The control circuit shifts one of the on-off switching time and each measurement time for which one of the resistance values is measured so that the on-off switching time lies out of each measurement time.

A second gas concentration sensor may also be provided which has a solid electrolyte-made sensor element producing a sensor output indicative of a concentration of a specified gas component and a second heater to heat the sensor element up to a temperature at which the sensor element is activated to produce the sensor output correctly. The heater power supply control circuit works to turn on and off a power supply to the second heater cyclically. The sensor element resistance determining circuit works to measures a resistance value of the sensor element of the second gas concentration sensor in a cycle by changing one of a voltage applied to the second heater and a current flowing through the second heater instantaneously, monitoring a change in the one of the voltage and the current, and calculating the resistance value of the second gas concentration sensor as a function of the change. The heater control variable determining circuit determines a heater control variable, which is used in the heater power supply control circuit to define an on-time for which the power supply to the second heater is to be turned on and an off-time for which the power supply to the second heater is to be turned off, as a function of a difference between the resistance value of the second gas concentration sensor and a target value. The control circuit determines whether an on-off switching time at which the power supply to the second heater is to be switched on or off will overlap with a measurement time for which the resistance value of the second gas concentration sensor is to be measured. When it is determined that the on-off switching time will overlap with the measurement time, the control circuit shifts one of the on-off switching time and the measurement time.

A peak hold circuit may be provided which works to hold a peak of the change in the one of the voltage and the current for use in calculating the resistance value. The measurement time is a time for which the peak is held by the peak hold circuit.

The sensor element resistance determining circuit may pick up the change in the one of the voltage and the current through an A/D converter. The measurement time contains a time for which the change is picked up through the A/D converter.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 20 is a time chart which shows a wave form of a sweeping current when occurs at the same time as power supply to a heater is switched on.

DESCRIPTION OF THE PREFERRED EMBODIMENTS

Figure 1:
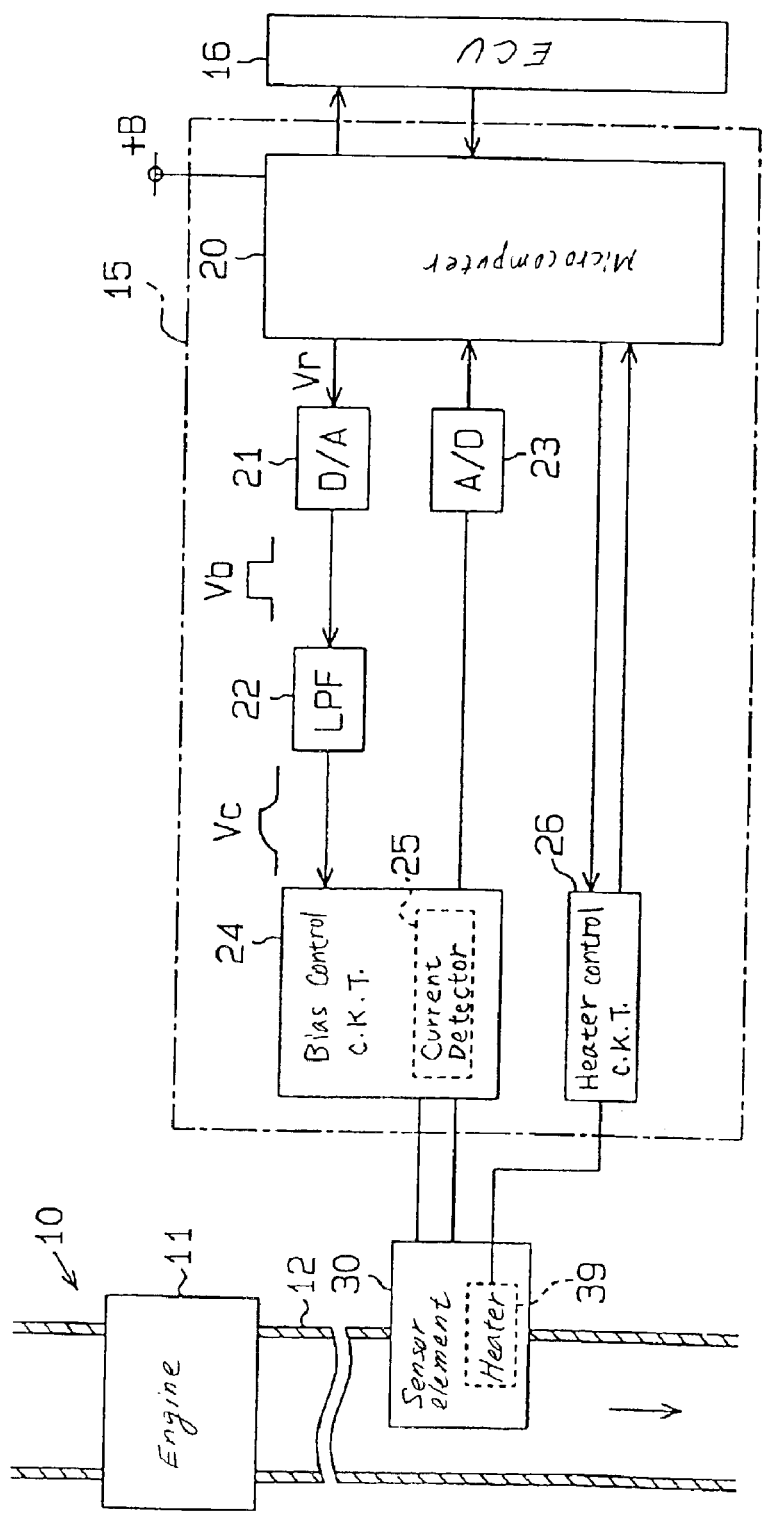
FIG. 1 is a block diagram which shows an air-fuel control system equipped with a heater control system according to the first embodiment of the invention.

Referring now to the drawings, wherein like numbers refer to like parts in several views, particularly to FIG. 1, there is shown a gas sensor control system according to the first embodiment of the invention which is installed in an air-fuel ratio measuring device 15 used with an air-fuel ratio control system for automotive vehicles. The air-fuel ratio control system is designed to control the quantity of fuel injected into an internal combustion engine as a function of an output of the air-fuel ratio measuring device 15 under feedback (F/B) control to bring the air-fuel ratio into agreement with a target value. The air-fuel ratio measuring device 15 measures the concentration of oxygen ($O_2$) contained in exhaust gasses of the engine using an output of a limiting current oxygen sensor 30 (will be referred to as an A/F sensor below) and determines an air-fuel ratio. The air-fuel ratio measuring device 15 also has installed therein a heater control system which works to determine the impedance of a sensor element of the A/F sensor 30 and control the power supply to a heater built in the A/F sensor 30 for ensuring desired activation of the A/F sensor 30.

In FIG. 1, the air-fuel ratio measuring device 15 includes a microcomputer 20. The microcomputer 20 communicates with an electronic control unit (ECU) 16 which works as an engine control unit and performs a fuel injection control operation and an ignition control, operation. The A/F sensor 30 is installed in an exhaust pipe 13 extending from a body 11 of the engine 10 and responsive to application of voltage from the microcomputer 20 to output an limiting current signal whose level changes linearly in proportion to the concentration of oxygen contained in the exhaust gasses.

The microcomputer 20 consists essentially of a CPU, a ROM, a RAM, etc. and executes a given control program to control a bias control circuit 24 and a heater control circuit 26 as will be described later in detail. The microcomputer 20 connects with a terminal+B of a storage battery installed in the vehicle and operates with a power supply therefrom.

The A/F sensor 30 is implemented by a so-called laminated sensor made of a lamination of a sensor element and a heater.

Figure 2:
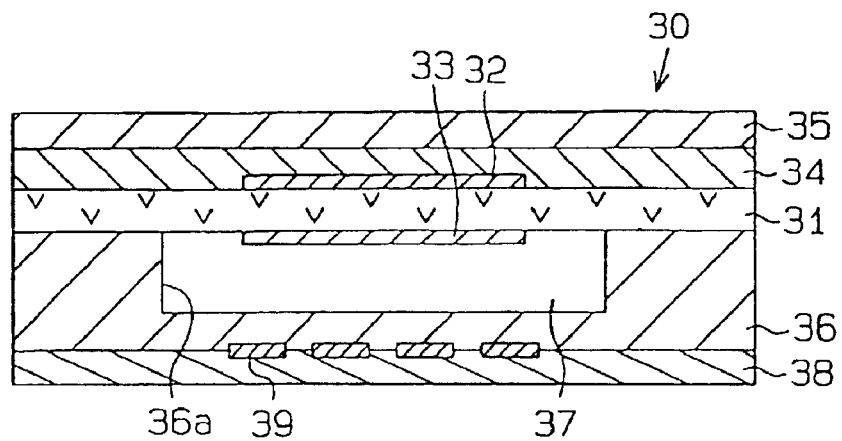
FIG. 2 is a longitudinal sectional view which shows an air-fuel ratio sensor in which a heater is controlled by the heater control system of FIG. 1.

An internal structure of the A/F sensor 30 will be described with reference to FIG. 2. FIG. 2 is a longitudinal sectional view as taken along a line extending in a lengthwise direction of the A/F sensor 30. The A/F sensor 30 is made of a lamination of a solid electrolyte layer 31, a porous diffusion resistance layer 34, a gas shield layer 35, a spacer 36, and a heater substrate 38. The solid electrolyte layer 31 is formed by an oxygen ion conductive layer made of a partially stabilized zirconia and has installed on opposed surfaces thereof a target gas electrode 32 and a reference gas electrode 33. The target gas electrode 32 is exposed to a target gas or exhaust gases of the engine 10. The reference gas electrode 33 is exposed to the air within a reference gas chamber 37. The air is used as a reference gas in determination of concentration of oxygen contained in the exhaust gasses. The porous diffusion resistance layer 34 is made of an alumina ceramic having a porosity of approximately 10%. The gas shield layer 35 is made of a dense alumina ceramic impermeable to gasses. The spacer 36 is made of a dense alumina ceramic which has an electric isolation property and is impermeable to gasses. The spacer 36 has formed therein a groove 36a working as the reference gas chamber 37. The heater substrate 38 is attached to the spacer 36 which has a heater 39 disposed in a surface thereof. The heater 39 generates heat with a power supply.

Referring back to FIG. 1, the air-fuel ratio measuring device 15 also includes a D/A converter 21, a low-pass filter 22, and an A/D converter 23. The microcomputer 20 provides a bias command signal Vr to the D/A converter 21 for applying the voltage to the A/F sensor 30. The D/A converter 21 converts the input into an analog signal V1 and outputs it to the low-pass filter 22. The low-pass filter 22 removes high-frequency components from the analog signal V1 to produce a voltage signal V2 which is, in turn, inputted to the bias control circuit 24. The bias control circuit 24 is responsive to the voltage signal V2 to selectively apply an air-fuel ratio measuring voltage and a sensor element impedance measuring voltage, as will be described later in detail, to the A/F sensor 30. Specifically, when it is required to measure the air-fuel ratio using the A/F sensor 30, the voltage selected as a function of the measured air-fuel ratio is applied to the A/F sensor 30. Alternatively, when it is required to measure the impedance of a sensor element (i.e., the solid electrolyte layer 31) of the A/F sensor 30, the sensor element impedance measuring voltage having a given frequency and a given time constant is applied to the A/F sensor 30 in the form of a single shot. The impedance of the sensor element will also be refereed to as a sensor element impedance below.

The bias control circuit 24 includes a current measuring circuit 25. The A/F sensor 30, when applied with the voltage, produces a limiting current as a function of an oxygen content in exhaust gasses. The current measuring circuit 25 measures the limiting current outputted from the A/F sensor 30. An output of the current measuring circuit 25 is inputted to the microcomputer 20 through the A/D converter 23.

The heater control circuit 26 is responsive to a control signal from the microcomputer 20 to control a power supply to the heater 39 based on the sensor element impedance of the A/F sensor 30. The heater control circuit 26 provides a heater control signal whose frequency is 10 Hz to control an on-time for which the heater 39 is turned on or energized within each cycle of approximately 100 ms.

Figure 3:
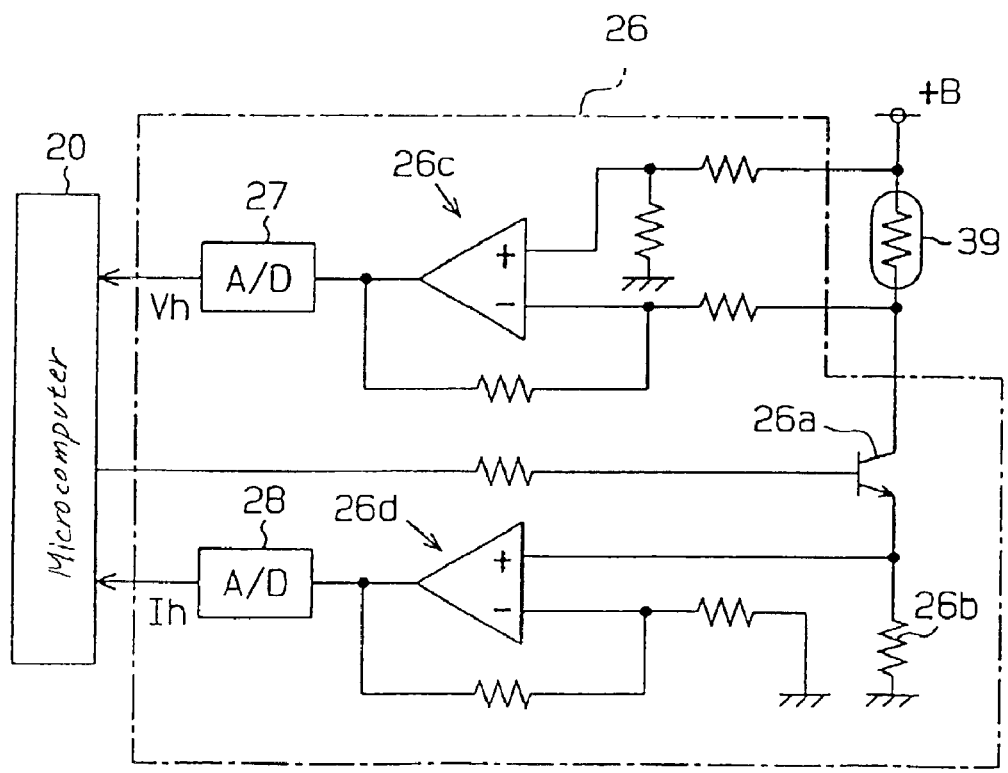
FIG. 3 is a circuit diagram which shows a circuit structure of a heater control circuit.

FIG. 3 shows an internal structure of the heater control circuit 26.

The heater control circuit 26 is connected at one end to the terminal+B of the storage battery mounted in the vehicle and at the other end to a collector of a transistor 26a. The transistor 26a is coupled at an emitter to ground through a heater current measuring resistor 26b. A potential difference (referred to as a heater voltage Vhe below) between ends of the heater 39 is inputted through an operational amplifier 26c and an A/D converter 27 to the microcomputer 20. The current flowing through the heater 39 (referred to as a heater current Ihe below) is measured as a function of a potential difference between ends of the heater current measuring resistor 26b and inputted to the microcomputer 20 through an operational amplifier 26b and an A/D converter 28.

When the heater control signal is switched from an off to an on state, the microcomputer 20 initiates an interruption program and determines times the heater voltage Vhe and the heater current Ihe are to be measured. Usually, at a time when the heater control signal is switched on, a time delay occurs in rising of the heater current Ihe. The times the heater voltage Vhe and the heater current Ihe are to be measured are, thus, determined taking such a delay into consideration.

The operation of the air-fuel ratio measuring device 15 will be described below.

Figure 4:
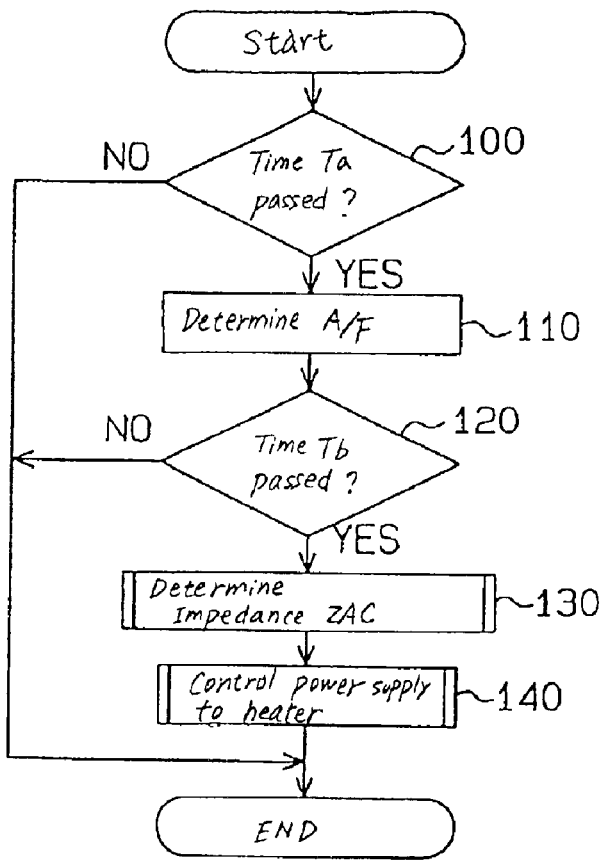
FIG. 4 is a flowchart of a main program performed to control a power supply to a heater.

FIG. 4 is a flowchart of a maim program performed by the microcomputer 20 upon turning on thereof.

After entering the program, the routine proceeds to step 100 wherein it is determined whether a preselected period of time Ta has passed since previous measurement of the air-fuel ratio or not. The preselected period of time Ta corresponds to a measurement cycle of the air-fuel ratio and is, for example, 4 ms. If a NO answer is obtained in step 100, then the routine repeats step 100. Alternatively, if a YES answer is obtained, then the routine proceeds to step 110 for measuring the air-fuel ratio.

In step 110, the microcomputer 20 applies the voltage across the electrodes 32 and 33 of the A/F sensor 30 to measure a sensor current (i.e., a limiting current) flowing therethrough using the current measuring circuit 25, determines an input voltage as a function of the sensor current, and applies it across the electrodes 33 and 34 of the A/F sensor 30. The microcomputer 20 converts the sensor current into a corresponding air-fuel ratio by look-up using a given current-A/F ratio map and outputs it to the ECU 16.

The routine proceeds to step 120 wherein it is determined whether a preselected period of time Tb has passed or not since the sensor element impedance ZAC, as will be discussed later in detail, was measured previously. The preselected period of time Tb corresponds to a measurement cycle of the sensor element impedance ZAC and is determined depending upon, for example, operating conditions of the engine 10. For example, when the engine 10 is in a normal operating condition in which a change in air-fuel ratio is relatively small, Tb=2 sec. When the engine 10 is in a start-up and transient conditions in which the air-fuel ratio changes greatly, Tb=128 msec.

If a YES answer is obtained in step 120, then the routine proceeds to step 130 wherein the sensor element impedance ZAC is determined using a so-called sweep method. The routine proceeds to step 140 wherein a power supply to the heater 39 is controlled. Alternatively, if a NO answer is obtained in step 120, then the routine returns back to step 100. The operations in step 130 and 140 will be discussed in detail below with reference to FIGS. 5 and 6, respectively.

Figure 5:
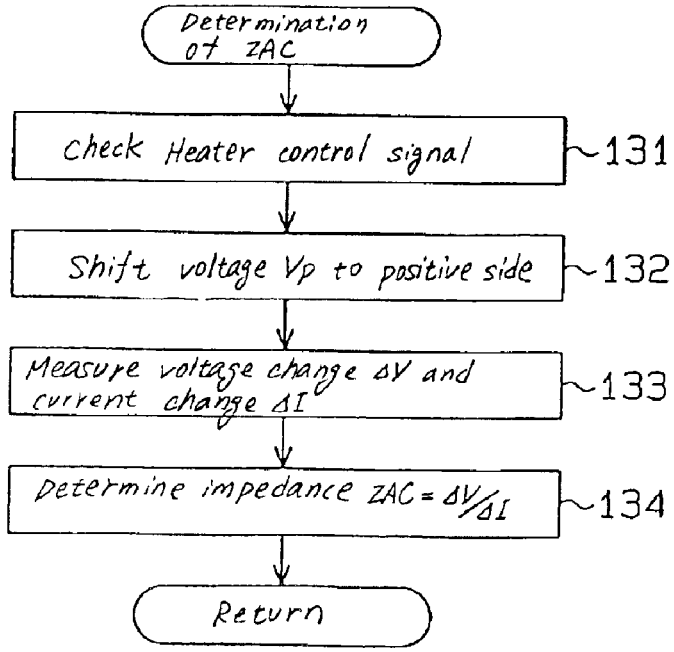
FIG. 5 is a flowchart of a subprogram used to determine the impedance of a sensor element.

After entering step 130, the routine proceeds to step 131 shown in FIG. 5 wherein the heater control signal is checked for inhibiting the heater 39 from being switched between on and off during measurement of the sensor element impedance ZAC.

The measurement of the sensor element impedance ZAC using the sweep method is usually achieved by shifting the voltage to be applied to the A/F sensor 30 either to a positive side or a negative side instantaneously. The switching between the on and off states of the heater 39 during the shifting of the voltage applied to the A/F sensor 30 will cause electric noises to be added to an electric circuit line extending through the sensor element, thereby resulting in an error in measuring the sensor element impedance ZAC. Such an error arises frequently, especially in a case where a harness extending to the sensor element (i.e., the electrodes 32 and 33) and a harness leading to the heater 39 are tied together. In order to avoid this problem, the microcomputer 20 monitors a time when the heater 39 is turned on or off and performs either of operations, as discussed below, to inhibit the heater 39 from being switched between the on and off states during measurement of the sensor element impedance ZAC.

(1) When it is determined that the on-off switching of the heater 39 will occur during measurement of the sensor element impedance ZAC, the measurement of the sensor element impedance ZAC is initiated after completion of the on-off switching of the heater 39.

(2) When it is determined that the on-off switching of the heater 39 will occur during measurement of the sensor element impedance ZAC, the on-off switching of the heater 39 is prohibited until completion of the measurement of the sensor element impedance ZAC by prolonging the on-time or the off-time of the heater 39 temporarily.

Subsequently, the routine proceeds to step 132 wherein the output of the bias command signal Vr is controlled to change a voltage Vp now provided to the A/F sensor 30 instantaneously to the positive side, thereby applying a sensor element impedance measuring voltage to the A/F sensor 30. The applied duration of the sensor element impedance measuring voltage is several tens to one hundred $\mu$sec. in light of frequency characteristics of the A/F sensor 30.

The routine proceeds to step 133 wherein a change $\Delta V$ in voltage Vp and a change $\Delta I$ in sensor current measured by the current measuring circuit 25 are determined. The routine proceeds to step 134 wherein the sensor element impedance ZAC is calculated using the voltage change a $\Delta V$ and the current change $\Delta I$ according to the relation of ZAC=$\Delta V/\Delta I$. The routine returns back to the program of FIG. 4.

Figure 7:
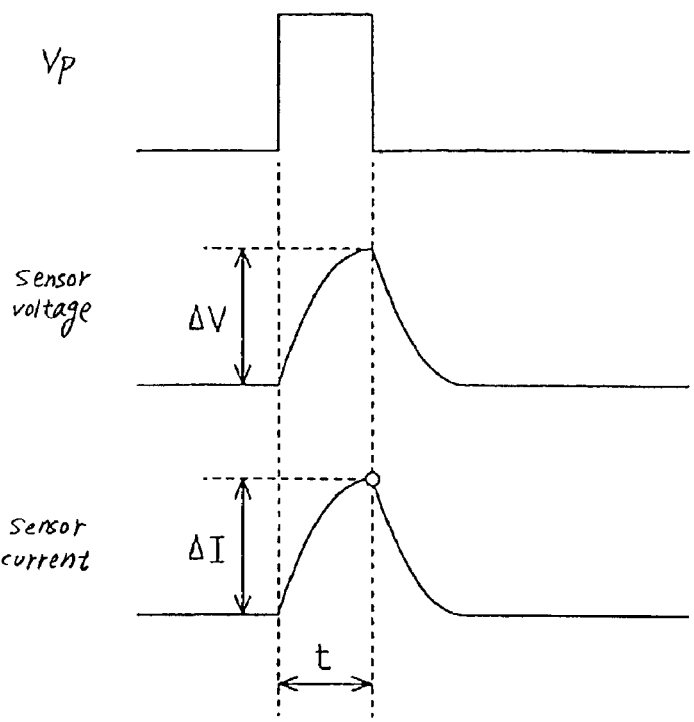
FIG. 7 is an illustration which shows changes in voltage developed at a sensor and a current flowing through the sensor.

The measurement of the sensor element impedance ZAC is, as discussed above, achieved by elevating the voltage Vp being applied to the A/F sensor 30 instantaneously, as shown in FIG. 7, to produce the sensor element impedance measuring voltage having a given time constant. After a lapse of a time t following application of the sensor element impedance measuring voltage to the A/F sensor 30, the peak of a current output from the A/F sensor 30 appears. This rise in the current output is measured as the current change $\Delta I$ and used to determine the sensor element impedance ZAC along with the voltage change $\Delta V$. The application of the sensor element impedance measuring voltage to the A/F sensor 30 is accomplished through the low-pass filter 22 and the bias control circuit 24, thereby avoiding an excessive rise in the current output from the A/F sensor 30, which results in improved measurement accuracy of the sensor element impedance ZAC.

The determination of the sensor element impedance ZAC may alternatively be accomplished by producing a change in current flowing through the A/F sensor 30 and measuring a resulting change in voltage applied across the A/F sensor 30.

Figure 8:
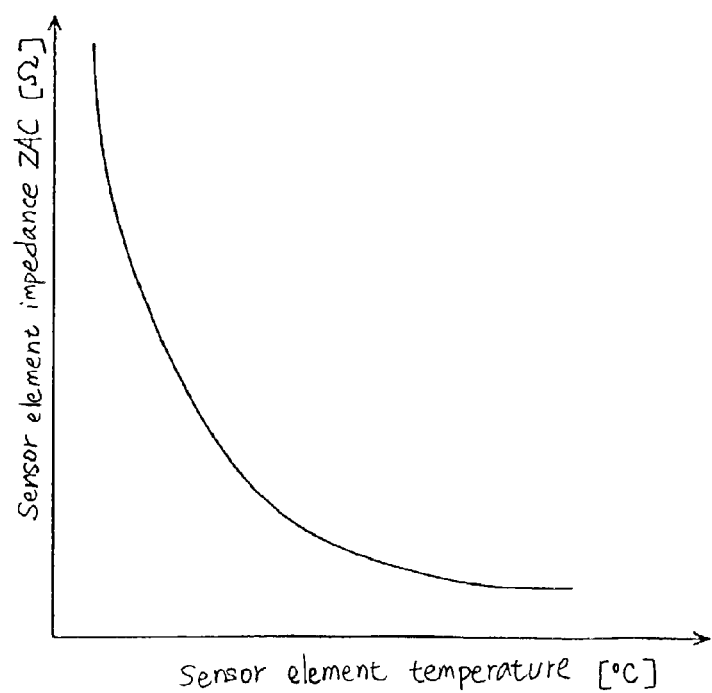
FIG. 8 is a graph which shows a relation between a sensor element impedance and a sensor temperature.

The sensor element impedance ZAC bears a relation, as shown in a graph of FIG. 8, to the temperature of the sensor element. The graph shows that the sensor element impedance ZAC increases greatly as the temperature of the sensor element decreases.

The determination of the sensor element impedance ZAC may alternatively be achieved by changing the current flowing through the sensor element instantaneously to measure the voltage change $\Delta V$ and a peak current (or the current change $\Delta I$).

The control of power supply to the heater 39 performed in step 140 in FIG. 4 will be described below with reference to FIG. 6. The heater control circuit 36 works to regulate the power supply to the heater 39 under feedback control so that the temperature of the sensor element of the A/F sensor 30 may be kept at a target value of 700° as a function of a variation in sensor element impedance ZAC.

Figure 6:
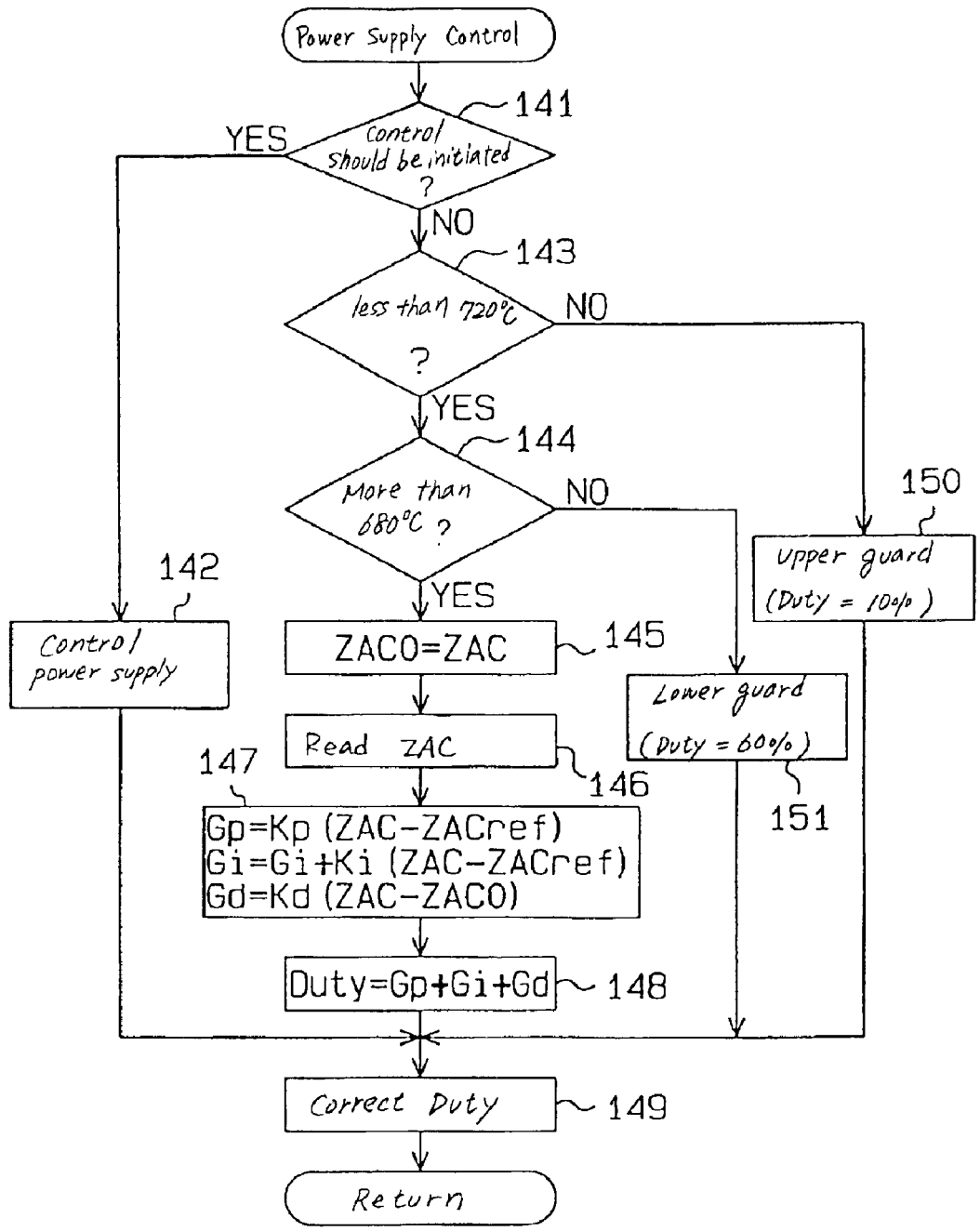
FIG. 6 is a flowchart of a subprogram used to provide a duty-controlled power supply control signal.

After entering step 140, the routine proceeds to step 141, as shown in FIG. 6, wherein it is determined whether a condition in which the control of power supply to the heater 39 should be initiated is met or not. For example, it is determined whether the sensor element impedance ZAC is greater than or equal to 50 $\Omega$ or not. Usually, immediately after start-up of the engine 10, the temperature of the A/F sensor 30 is low, so that the sensor element impedance ZAC is high. In this case, it is determined in step 141 that the control of power supply to the heater 39 should be initiated.

If a YES answer is obtained in step 141 meaning that the control of power supply to the heater 39 should be initiated, the routine proceeds to step 142 wherein a duty cycle-controlled signal (i.e., the heater control signal), which will also be referred to as a heater power supply control signal below), provided to turn on and off the transistor 26a in the heater control circuit 26 is kept in duty cycle at 100% to supply the power to the heater 39 fully.

The routine proceeds to step 149 wherein the duty cycle is corrected in a manner, as described later in detail, and returns back to the program of FIG. 4.

Alternatively, if the temperature of the sensor element has already risen, a NO answer is obtained in step 141. The routine, thus, proceeds to step 143 wherein it is determined whether the temperature of the sensor element (will also called a sensor element temperature hereinafter) is less than 720° C. or not. The sensor element temperature is calculated as a function of the sensor element impedance ZAC. If a YES answer is obtained, then the routine proceeds to step 144 wherein it is determined whether the sensor element temperature is greater than or equal to 680° C. or not. Specifically, it is determined through steps 143 and 144 whether the sensor element temperature falls within a controlled range of ±20° C. across 700° C. that is the target sensor element temperature or not. If the sensor element temperature falls within the controlled range, then the routine proceeds to step 145 wherein the duty cycle of the duty cycle-controlled signal is determined in a known PID control manner. Specifically, in step 145, the sensor element impedance ZAC as measured one program cycle earlier is defined as ZAC0. The routine proceeds to step 146 wherein the sensor element impedance ZAC, as determined in the current execution cycle of the program of FIG. 5, is read out of the memory. The routine proceeds to step 147 wherein a proportional term Gp, an integral term Gi, and a differential term Gd are determined using the following relations.

$$Gp=Kp \cdot (ZAC-ZACref)$$

$$Gi=Gi+Ki \cdot (ZAC-ZACref)$$

$$Gd=Kd \cdot (ZAC-ZAC0)$$

where Kp is a proportional constant, Ki is an integral constant, Kd is a differential constant., and ZACref is a target sensor element impedance corresponding to a target temperature of 700° C. at which the sensor element is to be kept.

The routine proceeds to step 148 wherein the proportional term Gp, the integral term Gi, and the differential term Gd are summed up to determine the duty cycle DUTY of the duty cycle-controlled signal (i.e., DUTY=Gp+Gi+Gd).

The routine proceeds to step 149 wherein the duty cycle DUTY is corrected in a manner as described later and returns back to the main program of FIG. 4.

Alternatively, if the sensor element temperature lies out of the controlled range of 700° C.±20° C., the routine proceeds either to step 150 or to step 151. Specifically, if the sensor element temperature is greater than or equal to 720° C., the routine proceeds to step 150 wherein the duty cycle DUTY is guarded with an upper limit of 10%. Specifically, a maximum value of the duty cycle Duty is restricted to 10% or less. If the sensor element temperature is lower than 680° C., then the routine proceeds to step 151 wherein the duty cycle DUTY is guarded with a lower limit of 60% so that it is restricted to 60% or more. This causes the duty cycle DUTY to be controlled in a direction in which a change in sensor element temperature or sensor element impedance ZAC is reduced. The upper and lower limits serve as guard values for guarding the duty cycle DUTY from an undesirable change. The guard values are not limited to 10% and 60% and may be set to values that may not be thought of as causing damage to the A/F sensor 30 in design.

The correction of the duty cycle DUTY made in step 149 will be described below in detail.

The correction of the duty cycle DUTY is achieved by comparing a preselected reference heater power with a power actually used in the heater 39. Specifically, the duty cycle DUTY is multiplied by a correction value that is the quotient of the reference heater power by the actual heater power (i.e., reference heater power/actual heater power). The determination of the actual heater power requires measurement of the heater voltage and heater current of the heater 39. This, however, result in an increase in operation load of the system. In order to alleviate this drawback, either of corrections, as discussed below, may be performed.

1 Duty Cycle Correction Using Heater Voltage

If the heater power, the heater voltage, the heater current, and the heater resistance are defined as W, V, I, and R, then $W=V \cdot I=V^2/R$. In a case where the heater resistance R may be though of as being constant, the correction value (reference heater power/actual heater power) may be given by (reference heater voltage)$^2$/(actual heater voltage)$^2$. The reference heater voltage is defined in advance as a voltage corresponding to the reference heater power. Therefore, the correction value may be calculated mathematically by measuring the voltage appearing across the heater 39. The duty cycle DUTY is corrected by multiplying it by the thus determined correction value.

Alternatively, in a case where the heater current I may be viewed to be constant, the correction value may be given by (reference heater voltage)/(actual heater voltage). Thus, the correction value is, like the above, determined by measuring the voltage appearing across the heater 39.

2 Duty Cycle Correction Using Heater Current

W is, as described above, given by the relation of $V \cdot I=V^2/R$. Thus, in a case where the heater resistance R may be though of as being constant, the correction value (reference heater power/actual heater power) may be given by (reference heater current)$^2$/(actual heater current)$^2$. The reference heater current is defined in advance as a current corresponding to the reference heater power. Therefore, the correction value may be calculated mathematically by measuring the current flowing through the heater 39. The duty cycle DUTY is corrected by multiplying it by the thus determined correction value Alternatively, in a case where the heater voltage V may be thought of as being constant, it is possible to define the correction value by (reference heater current)/(actual heater current). Thus the correction value is, like the above, determined by measuring the current flowing through the heater 39.

Either of the above operations enables the duty cycle DUTY of the duty cycle-controlled signal (i.e., the heater power supply control signal) provided to control the power supply to the heater 39 to be corrected without an unwanted increase in operation load of the system. Particularly, the current flowing through a circuit line extending through the heater 39 is usually constant. The use of the current in correcting the duty cycle DUTY, thus, serves to compensate for a variation in resistance of a harness leading to the heater 39.

Figure 9:
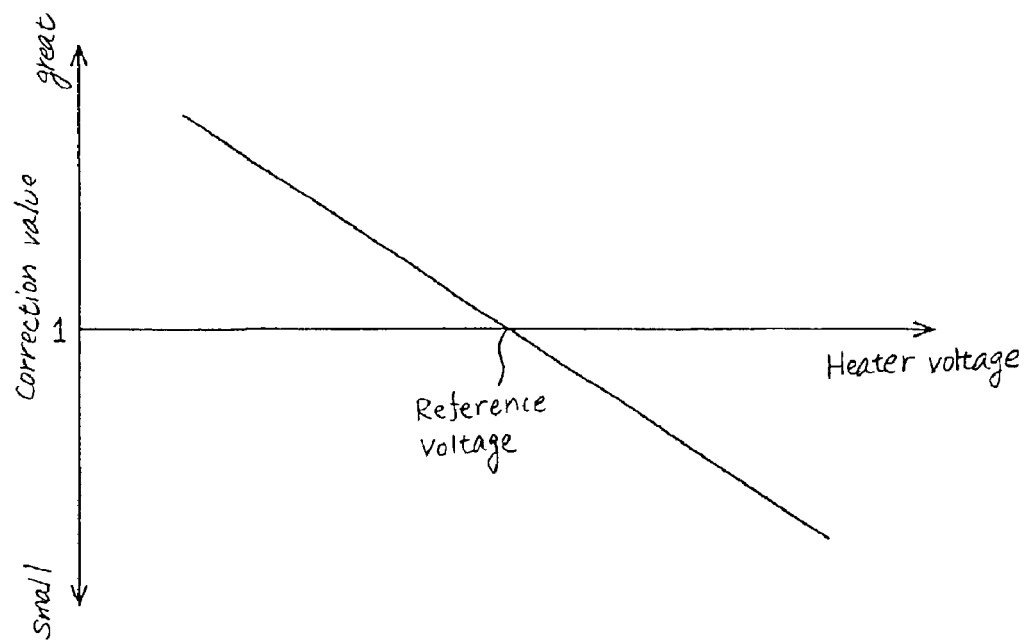
FIG. 9 is a map used to determine a correction value for a duty cycle of a heater power supply control signal.

The correction of the duty cycle DUTY may also be performed using a map, as shown in FIG. 9. Specifically, as the actual heater voltage rises, the correction value is decreased. The correction of the duty cycle DUTY using the heater current may also be achieved using a similar map. In this case, reflection of a voltage drop arising from the resistance of the harness on the map will result in improved system adaptability.

Figure 10A:
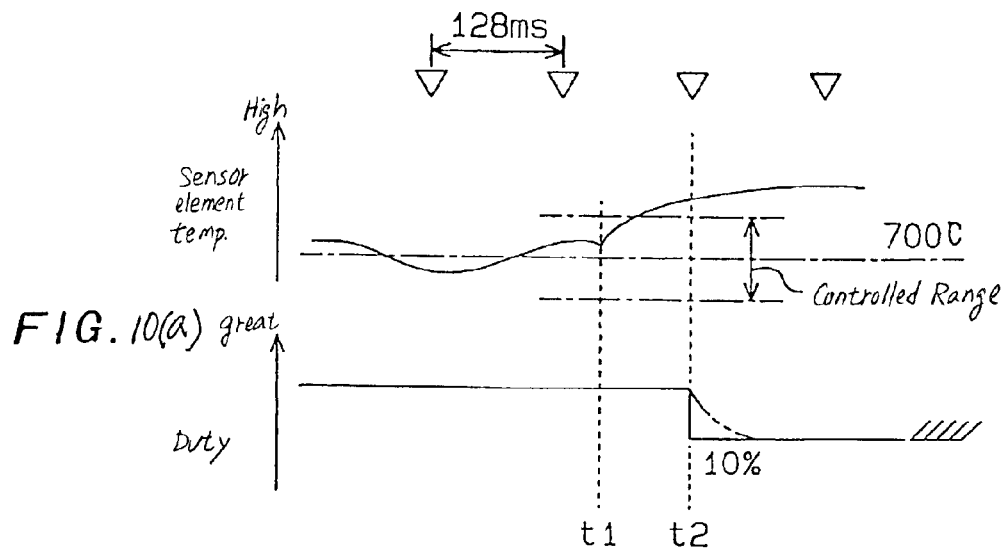
FIG. 10(a) illustrates for a case where the temperature of a sensor element rises rapidly subjected to the heat of exhaust gasses and is brought outside a controlled range.
Figure 10B:
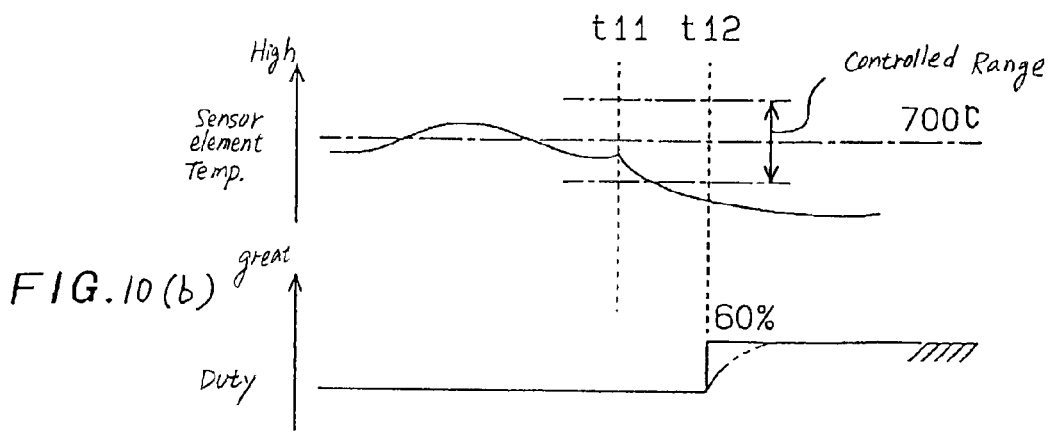
FIG. 10(b) illustrates for a case where the temperature of a sensor element drops rapidly subjected to a fuel cut and is brought outside a controlled range.

FIGS. 10(*a*) and 10(*b*) show the control of power supply to the heater 39 in cases where the temperature of the sensor element rises and drops rapidly, respectively. FIG. 10(*a*) illustrates for a case where the temperature of the sensor element rises (i.e., the sensor element impedance ZAC is decreased) quickly subjected to the heat of exhaust gasses and is brought outside the controlled range. FIG. 10(b) illustrates for a case where the temperature of the sensor element drops (i.e., the sensor element impedance ZAC is increased) rapidly subjected to a fuel cut and is brought outside the controlled range. "∇" indicates each start of the control of power supply to the heater 39 performed at a regular interval of, for example, 128 msec.

In FIG. 10(a), before time t1, the temperature of the sensor element is kept near a target of 700° C. under feedback control. If the temperature of the sensor element rises quickly at time t1 and is shifted out of the controlled range of 700° C.±20° C., the duty cycle DUTY of the heater power supply control signal provided to control the power supply to the heater 39 is, as described above, guarded with the upper limit of 10% at time t2. If the feedback control (i.e., the PID control) continues to be performed as it is after time t2, it will cause the duty cycle DUTY to change, as indicated by a broken line, slowly, thus, consuming an unwanted time until the duty cycle DUTY reaches a desired lower value, however, the quick decrease in duty cycle DUTY to the upper limit minimizes a control lag.

In FIG. 10(b), before time t11, the temperature of the sensor element is kept near the target under feedback control. If the temperature of the sensor element drops quickly at time t11 and is shifted out of the controlled range of 700° C.±20° C., the duty cycle DUTY of the heater power supply control signal is, as described above, guarded with the lower limit of 60% at time t12. If the feedback control (i.e., the PID control) continues to be performed as it is after time t12, it will cause the duty cycle DUTY to change, as indicated by a broken line, slowly, thus consuming an unwanted time until the duty cycle DUTY reaches a desired higher value, however, the quick increase in duty cycle DUTY to the lower limit, like the above, minimizes the control lag.

As apparent from the above discussion, the amount of power supply to the heater 39 (i.e., the duty cycle DUTY of the heater power supply control signal)) is controlled by the comparison between the reference heater power and the actual heater power. This allows the amount of power supply to be adjusted to a desired one quickly even if the heater power is changed by a change in output voltage of the power source for the heater 39 or a change in voltage applied directly to the heater 39 due to a change in resistance of the harness, for example, thus resulting in improved controllability of the power supply.

Additionally, use of the upper and lower limits of the duty cycle DUTY enables the control of the power supply to the heater 39 to follow a sudden change in temperature of the sensor element due to a temperature rise of exhaust gasses or a fuel cut quickly. Usually, determination of a duty cycle using the integral term in the PID control results in a control delay in response to a sudden change in temperature of the sensor element, but however, the control in this embodiment addresses such a problem. This avoids premature activation of the sensor element subjected to a lower temperature and damage of the sensor element subjected to a high temperature.

Figure 11:
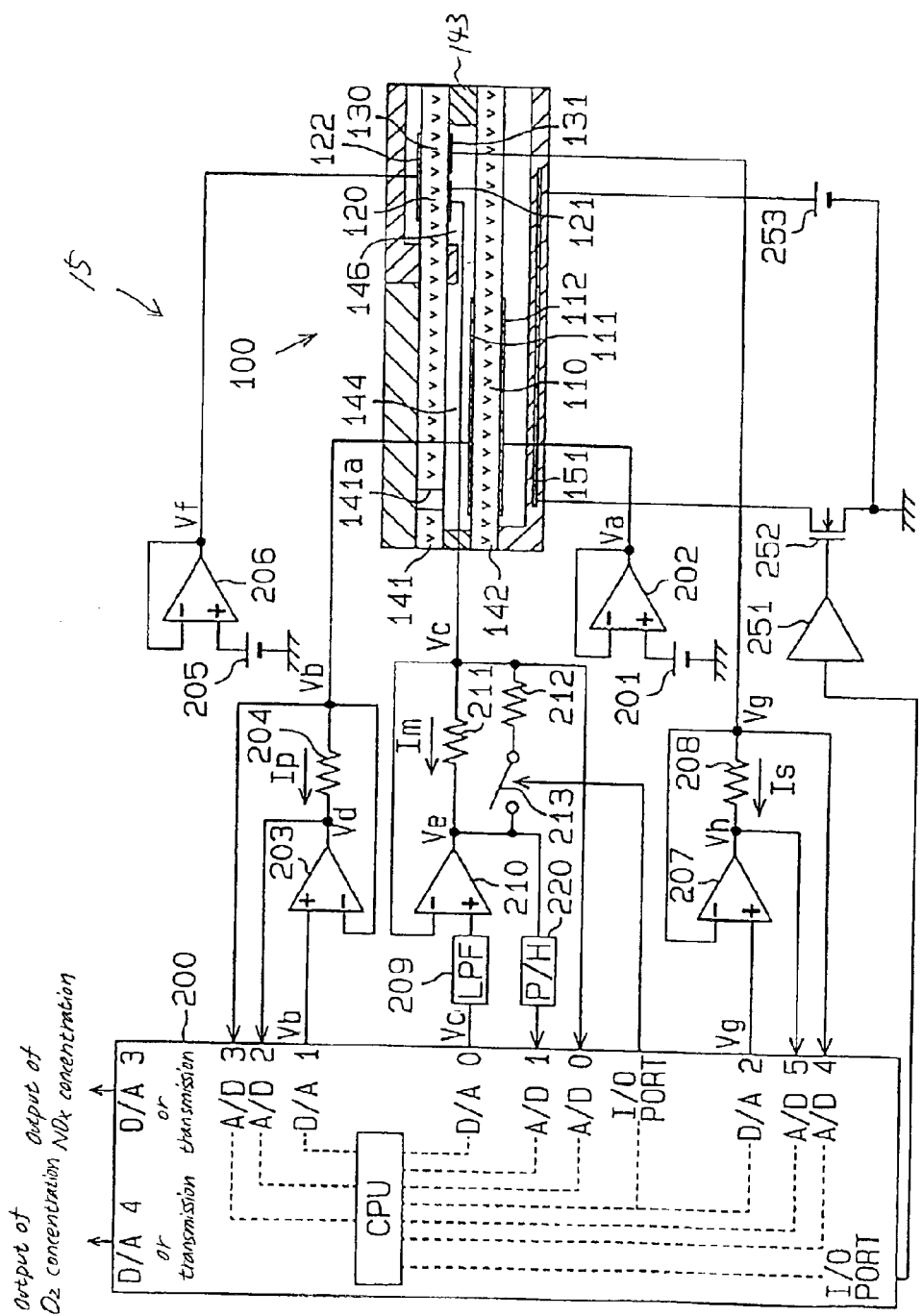
FIG. 11 is an air-fuel ratio measuring device equipped with a heater control system according to the second embodiment of the invention.

FIG. 11 shows an air-fuel ratio measuring device 15 according to the second embodiment which is designed to measure the concentration of NOx as well as $O_2$ contained in exhaust gasses of the engine.

Figure 12A:
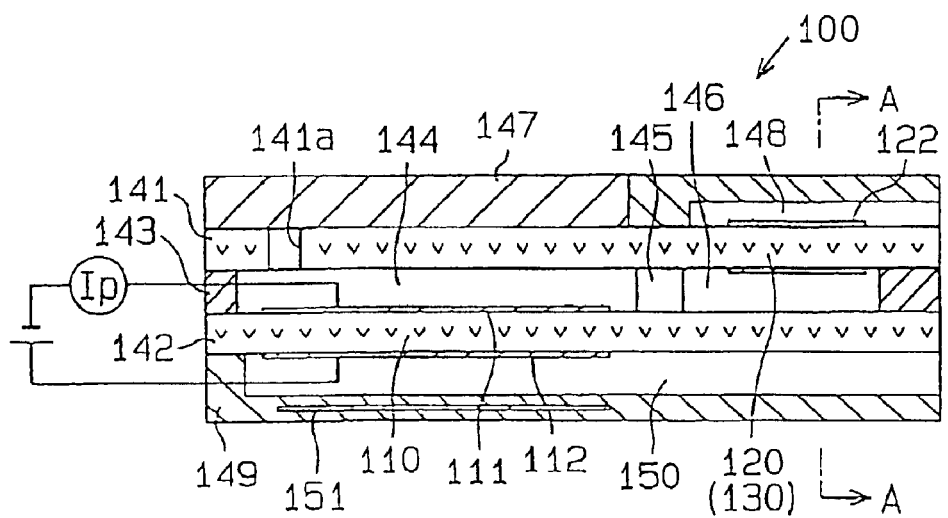
FIG. 12(a) is a longitudinal sectional view which shows a gas concentration sensor in which a heater is controlled by the heater control system of FIG. 11.
Figure 12B:
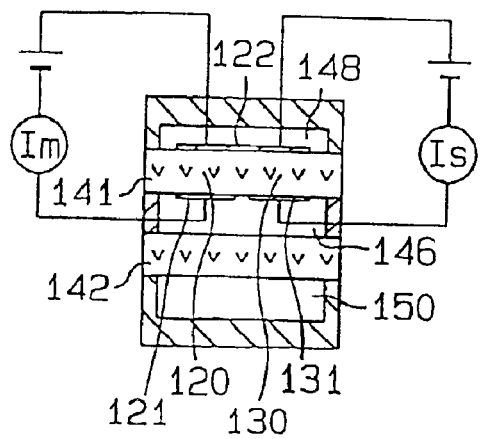
FIG. 12(b) is a lateral sectional view taken along the line A—A in FIG. 12.

The air-fuel ratio measuring device 15 includes a gas concentration sensor 100 that is of a so-called composition type having, as shown in FIGS. 12(a) and 12(b), a three-cell structure to measure the concentration of NOx and $O_2$ simultaneously.

The gas concentration sensor 100 includes generally solid electrolyte plates 141 and 142 made of an oxygen ion-conducting material. The solid electrolyte plates 141 and 142 are laid to overlap each other at a given interval through a spacer 143 made of an insulating material such as alumina. The solid electrolyte plate 141 has formed therein a pinhole 141a through which exhaust gasses flowing around the gas concentration sensor 100 are admitted into a first chamber 144. The first chamber 144 communicates with a second chamber 146 through an orifice 145 working as a diffusion path. On the solid electrolyte plate 141, a porous diffusion layer 147 is formed.

The solid electrolyte plate 142 has formed therein a pump cell 110 which is exposed to the first chamber 144. The pump cell 110 works to dissociate or ionize and pump thereinto oxygen molecules ($O_2$) contained the exhaust gasses admitted into the first chamber 144 and discharge them for measuring the concentration of oxygen ($O_2$) contained in the exhaust gasses and also to dissociate or ionize and pump oxygen molecules ($O_2$) within an air passage 150 into the first chamber 144 when the concentration of oxygen within the first chamber 144 is lower than a given level for keeping the concentration of oxygen within the first chamber 144 at the given level. The pump cell 110 has a pair of upper and lower electrodes 111 and 112 disposed on opposed surfaces of the solid electrolyte plate 142. The upper electrode 111 is exposed to the first chamber 144 and inactive with respect to NOx, that is, hardly decomposes NOx. The pump cell 110 works to pump $O_2$ molecules contained in the exhaust gasses out of the first chamber 144 and discharge them to the air passage 150 through the electrode 112.

A monitor cell 120 and a sensor cell 130 are also formed on the solid electrolyte plate 141. The monitor cell 120 and the sensor cell 130 are exposed to the second chamber 146. The monitor cell 120 works to produce an electromotive force or current upon application of the voltage as a function the concentration of oxygen ($O_2$) remaining within the second chamber 146. The sensor cell 130 serves to measure the concentration of NOx contained in the exhaust gasses having passed through the pump cell 110.

The monitor cell 120 and the sensor cell 130 are, as can be seen from FIG. 12(b), arranged in parallel at substantially the same location with respect to a flow of the exhaust gasses. The monitor cell 120 and the sensor cell 130 share an electrode 122 exposed to an air passage 148. Specifically, the monitor cell 120 is made up of the solid electrolyte plate 141, an electrode 121, and the common electrode 122. The sensor cell 130 is made up of the solid electrolyte plate 141, an electrode 131 and the common electrode 122. The electrode 121 of the monitor cell 120 is made of a noble metal such as Au-Pt which is inactive with respect to NOx, while the electrode 131 of the sensor cell 130 is made of a noble metal such as Pt which is active with respect to Nox.

An insulating layer 149 is disposed on a lower surface, as viewed in FIG. 12(a), of the solid electrolyte plate 142 to define the air passage 150. The insulating layer 149 has embedded therein a heater 151 for heating the whole of the sensor 100 up to a desired activation temperature.

In operation, when exhaust gasses containing $O_2$, NOx, $CO_2$, and $H_2O$ enter the first chamber 144 through the porous diffusion layer 147 and the pinhole 141a and are passing through the pump cell 110, application of voltage to the pump cell 110 through the electrodes 111 and 112 causes the exhaust gasses to undergo dissociation, so that the oxygen ($O_2$) is pumped into or out of the first chamber 144 as a function of the concentration of oxygen ($O_2$) within the first chamber 144 so as to keep the concentration of oxygen within the first chamber 144 constant. Since the upper electrode 111 of the pump cell 110 is, as described above, made of a metal which hardly decomposes NOx, when the concentration of oxygen within the first chamber 144 is higher than a desired level, only $O_2$ molecules within the first chamber 144 are ionized by the pump cell 110 without decomposing NOx, which are, in turn, discharged to the air passage 150. This causes a current (will also referred to as a pump cell current below) to be produced in the pump cell 110 as a function of the oxygen content of the exhaust gasses. EP0 987 546 A2, assigned to the same assignee as that of this application, teaches control of an operation of this type of gas sensor, disclosure of which is incorporated herein by reference.

The $O_2$ molecules in the exhaust gasses are usually not dissociated by the pump cell 110 completely, so that residual $O_2$ molecules flows into the second chamber 146 and reach the monitor cell 120. The application of given voltage to the monitor cell 120 through the electrodes 121 and 122 causes an output (will also be referred to as a monitor cell current below) to be produced as a function of the concentration of the residual oxygen. The application of given voltage to the sensor cell 130 through the electrodes 131 and 122 causes NOx molecules contained in the exhaust gasses to be decomposed or reduced, so that oxygen ions are produced and discharged to the air passage 148, thereby causing a current (also referred to as a sensor cell current or a NOx current below) to flow through the sensor 130 as a function of the concentration of NOx within the second chamber 146.

Referring back to FIG. 11, the air-fuel ratio measuring device 15 of the second embodiment has a shown electric structure. Note that in FIG. 11, the electrode 121 of the monitor cell 120 and the electrode 131 of the sensor cell 130 are illustrated as being arrayed adjacent to each other in a direction of flow of the exhaust gasses (i.e., a lengthwise direction of the sensor 100) for ease of visibility.

The air-fuel ratio measuring device 15 includes a control circuit 200. The control circuit 200 is implemented by a known microcomputer made up of a CPU, A/D converters, D/A converters, I/O ports, etc. and works to apply voltages to the cells 110, 120, and 130 through the D/A converters (D/A 0 to D/A 2). The control circuit 200 also picks up voltages appearing between terminals Vc and Ve, between terminals Vd and Vb, and between terminals Vg and Vh through the A/D converters (A/D 0 to A/D 5). The control circuit 200 measures the pump cell current and the sensor cell current to determine the concentration of $O_2$ and NOx contained in the exhaust gasses and outputs signals indicative thereof to the ECU 16, as shown in FIG. 1, through the D/A converters (D/A 4 and D/A 3).

The pump cell 110 is coupled at the electrode 112 with a reference power supply 201 through an operational amplifier 202 and at the electrode 111 with the control circuit 200 through an operational amplifier 203 and a current detecting resistor 204. The reference power supply 201 applies a reference voltage Va to the electrode 112. The control circuit 200 applies a command voltage Vb to the electrode 111. The application of the voltage Vb causes the pump cell 110 to produce a flow of current as a function of the concentration of oxygen contained in the exhaust gasses which is, in turn, detected through the current detecting resistor 204. Specifically, the control circuit 200 measures the voltages Vb and Vd appearing across the current detecting resistor 204 and determines the current flowing through the resistor 204 as the pump cell current Ip.

The monitor cell 120 and the sensor cell 130 are coupled at the common electrode 122 with a reference power supply 205 through an operational amplifier 206. The sensor cell 130 is coupled at the electrode 131 with the control circuit 200 through a current detecting resistor 208 and an operational amplifier 207. The reference power supply 205 applies a reference voltage Vf to the common electrode 122. The control circuit 200 applies a command voltage Vg to the electrode 131 of the sensor cell 130. The application of the voltage Vg causes the sensor cell 130 to produce a flow of current as a function of the concentration of NOx contained in the exhaust gasses which is, in turn, detected through the current detecting resistor 208. Specifically, the control circuit 200 measures the voltages Vg and Vh appearing across the current detecting resistor 208 and determines the current flowing through the resistor 208 as the sensor cell current Is.

The electrode 121 of the monitor cell 120 is applied with a command voltage Vc outputted from the control circuit 200 through a low-pass filter 209, an operational amplifier 210, and a current detecting resistor 211. The application of the voltage Vc causes the monitor cell 120 to produce a flow of current as a function of the concentration of oxygen remaining in the exhaust gasses within the second chamber 146 which is, in turn, detected through the current detecting resistor 211. Specifically, the control circuit 200 measures the voltages Vc and Ve appearing across the current detecting resistor 211 and determines the current flowing through the resistor 211 as the monitor cell current Im. The low-pass filter 209 is implemented by, for example, a primary filter made up of a resistor and a capacitor.

The control circuit 200 measures the impedance of the gas concentration sensor 100 (i.e., the sensor element impedance ZAC) through the monitor cell 120 in the sweep method. The measurement of the impedance is achieved by switching the command voltage Vc to either of the positive and the negative side instantaneously. The command voltage Vc is shaped by the low-pass filter 209 into a sine wave and then applied to the monitor cell 120. The frequency of this alternating voltage is preferably 10 kHz or more. The time constant of the low-pass filter 209 is on the order of 5 $\mu$sec. The control circuit 200 measures changes in voltage Vc and monitor cell current Im and determines the impedance of a sensor element (i.e., the monitor cell 120 in this embodiment) of the gas concentration sensor 100.

The monitor cell 120 and the sensor cell 130, as described above, share the electrode 122 with each other, thereby eliminating the need for reference voltage drivers one for each of the monitor cell 120 and the sensor cell 130 and resulting in a decrease in lead extending from the gas concentration sensor 100. The monitor cell 120 and the sensor cell 130 are arranged close to each other on the same solid electrolyte plate 141, thus leading to a greater concern about a leakage of current to the sensor cell 130 resulting in a decrease in accuracy of measuring the impedance. This problem is, however, eliminated by the use of the common electrode 122 to keep an electric potential appearing at the same side of the monitor cell 120 and the sensor cell 130 constant.

When it is required to monitor the concentration of oxygen remaining in the second chamber 146, the current flowing through the monitor cell 120 is no more than several $\mu$A, while a current of several mA flows through the monitor cell 120 when measuring the impedance. Thus, if a current measurable range is matched to the current used to measure the concentration of oxygen, it will cause the current used to measure the impedance to exceed the current measurable range greatly. Alternatively, if the current measurable range is matched to the current used to measure the impedance, it will cause a change in current used to measure the concentration of oxygen to be too small to ensure a desired accuracy of measurement of the current in the current measuring circuit 25. In order to avoid such a problem, the structure of this embodiment uses an additional resistor 212.

The resistor 212 is arranged in parallel to the current detecting current 211 together with a switch 213 made of, for example, a semiconductor switch. When it is required to measure the concentration of oxygen remaining in the second chamber 146, the control circuit 200 outputs an off-signal from the I/O port to open the switch 213, thereby allowing the monitor cell current Im to be measured through the current detecting resistor 211 having a several hundreds kΩ. Alternatively, when it is required to measure the impedance of the monitor cell 120, the control circuit 200 outputs an off-signal from the I/PO port to close the switch 213, thereby allowing the monitor cell current Im to be measured through a combination of the resistors 211 and 212 whose total resistance value is approximately several hundreds Ω.

The voltage Ve is inputted to the control circuit 200 through a peak-hold (P/H) circuit 220. When it is required to measure the impedance of the monitor cell 120, the control circuit 200 sets a peak-holding time during the voltage Ve has a peak thereof.

The CPU of the control circuit 200 outputs the duty cycle-controlled signal or heater power control signal having the duty cycle DUTY from the I/O port to a MOSFET driver 251 to control the power supplied from a power source 253 (e.g., the battery installed in the vehicle) to the heater 151 through PWM control.

Figure 13:
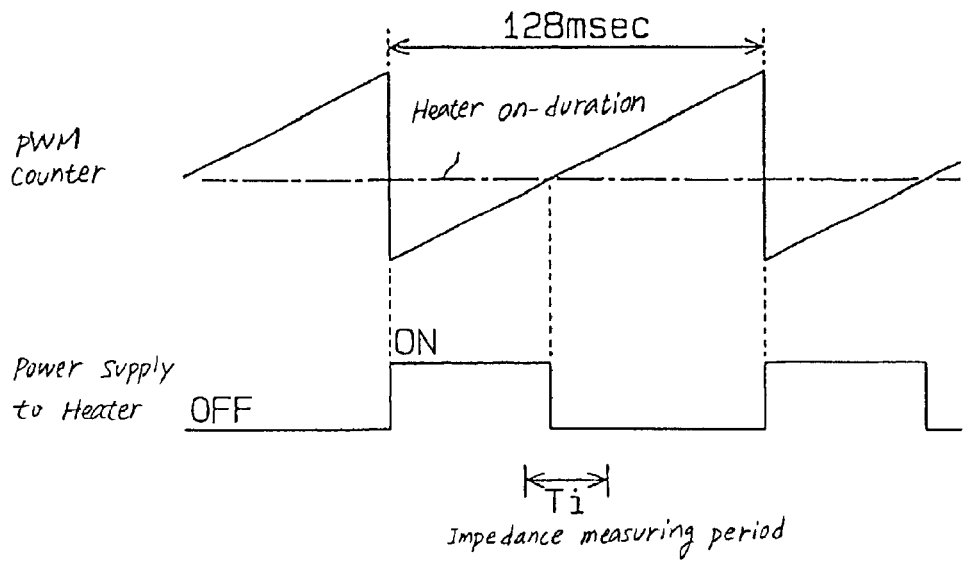
FIG. 13 is an illustration which shows a relation between a heater on-duration and an impedance measuring period.

FIG. 13 shows a control operation of the heater 151. The control circuit 200 has installed therein a PWM (Pulse Width Modulation) counter which counts up counter values and is reset at a regular time interval of 128 msec. which is equivalent to a cycle in which the sensor element impedance ZAC is to be measured.

Each time the control circuit 200 determines the duty cycle DUTY, it stores a heater on-duration defined by the duty cycle DUTY in a register. When the heater on-duration expires in the PWM counter, the power supply to the heater 151 is cut. Upon each reset of the PWM counter, the power supply to the heater 151 is resumed.

Figure 20:
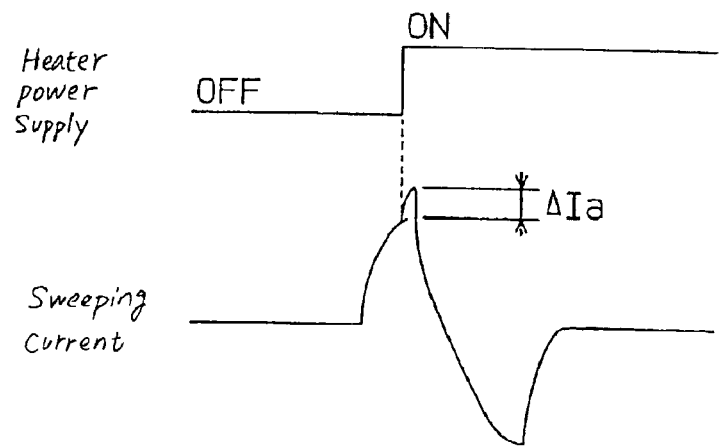

If the power supply to the heater 151 (i.e., the heater power supply control signal) is, as shown in the drawing, switched from on to off in a period of time Ti during which the sensor element impedance ZAC is to be measured, it may cause, as described above, an electric noise to be added to an electric line extending through the sensor element, thus impinging upon the measurement of the sensor element impedance ZAC adversely. For instance, an error ΔIa, as shown in FIG. 20, is added to a sweeping current resulting from a sweep of the voltage applied to the heater 151, which causes the P/H circuit 220 to hold an incorrect peak of the voltage Ve undesirably In order to avoid this problem, the control circuit 200 works to shift either of an on-switching time at which the power supply to the heater 151 is to be switched on and an off-switching time at which the power supply to the heater 151 is to be switched off when it is determined that the on-off switching of the power supply to the heater 151 will take place in the impedance measuring period Ti during which the sensor element impedance ZAC is to be measured. This operation will be described below in detail.

Figure 14:
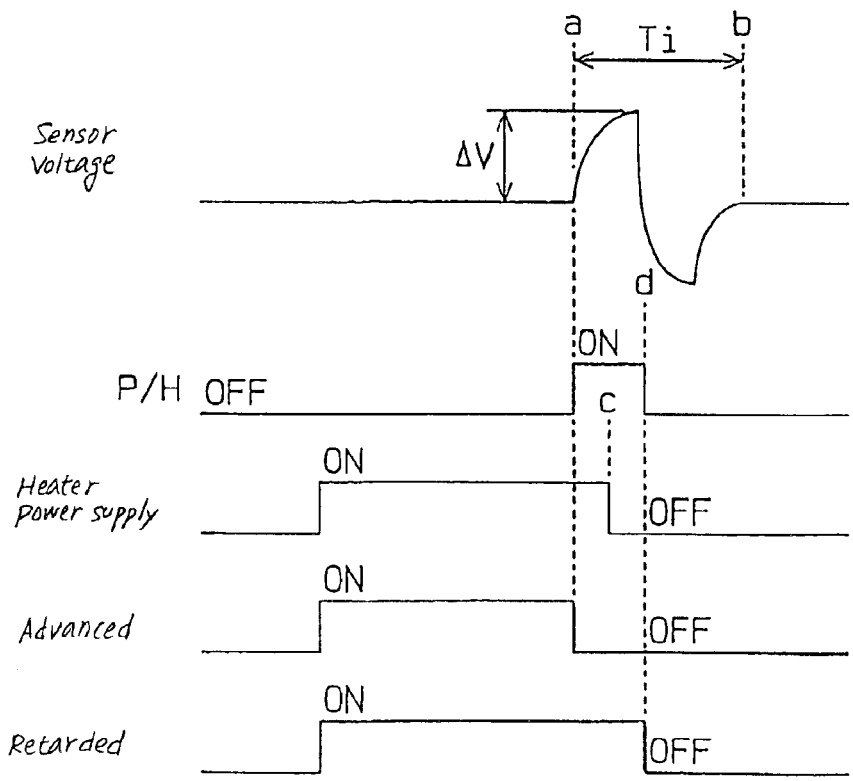
FIG. 14 is a time chart which shows cases where an on-off switching time of a heater power supply control signal is advanced and retarded, respectively, to avoid overlapping between the on-off switching time and a period of time during which an impedance of a sensor element is to be measured.

In FIG. 14, the impedance measuring period Ti is defined between times a and b. When it is required to measure the sensor element impedance ZAC, the control circuit 200 produces a sweep of the voltage applied to the gas concentration sensor 100, that is, a change ΔV in voltage applied across the monitor cell 120. In the illustrated case, the power supply to the heater 151 is switched from on to off at time c in the impedance measuring period Ti. The control circuit 200, thus, advances or retards, as can be seen from the drawing, the off-switching time at which the power supply to the heater 151 is to be cut before or after the change ΔV in voltage applied across the monitor cell 120. This is because it is essential for determination of the sensor element impedance ZAC to measure the voltage change ΔV and a resulting change in monitor cell current Im correctly, and it is important to prohibit the on-off switching of the power supply to the heater 151 from taking place until the voltage applied to the monitor cell 120 reaches its peak. In this embodiment, the control circuit 200 shifts the on-switching time or the off-switching time out of the control circuit 200 sets the peak-holding time of the P/H circuit 220 defined between times a and d.

Figure 15:
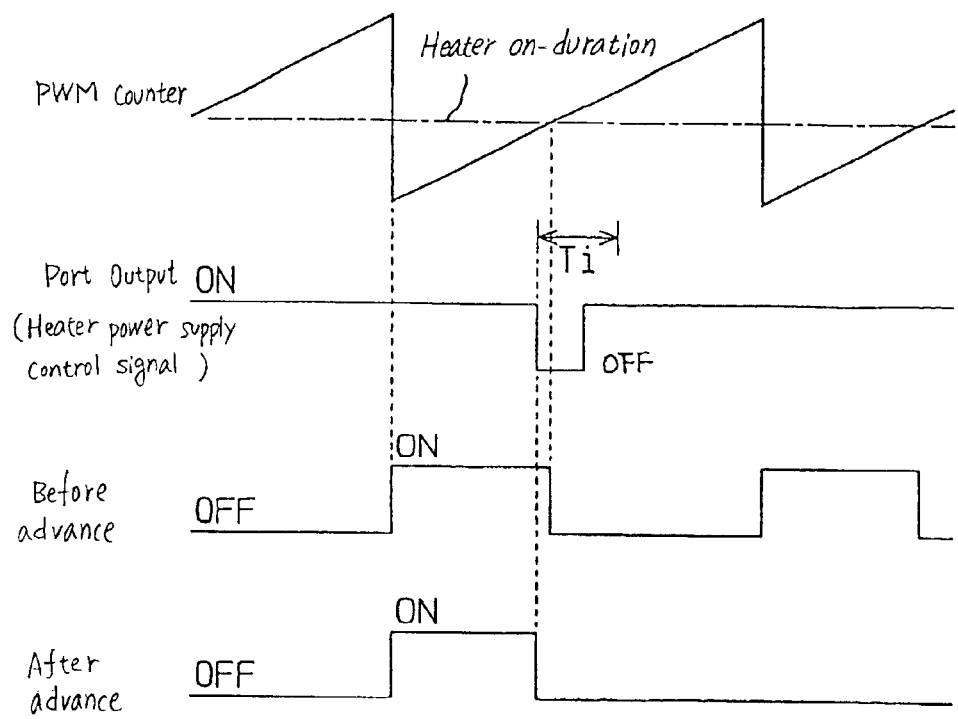
FIG. 15 is a time chart which shows an example of control of power supply to a heater.

The advancing or retarding of the on-off switching of the power supply to the heater 151 may be achieved by controlling the heater power supply control signal (i.e., the duty cycle-controlled signal) outputted from the I/O port of the control circuit 200 to the MOSFET 252 through the MOSFEET driver 251. For example, in a case where the power supply to the heater 151 is, as shown in FIG. 15, switched from on to off within the impedance measuring period Ti, the control circuit 200 stops outputting the heater power supply control signal from the I/O port temporarily, thereby advancing, as clearly shown in the lowermost portion of FIG. 15, the off-switching time at which the power supply to the heater 151 is to be cut. Alternatively, the control circuit 200 may shorten or prolong the heater on-duration counted by the PWM counter, thereby advancing or retarding the on-off switching of the power supply to the heater 151.

Figure 16:
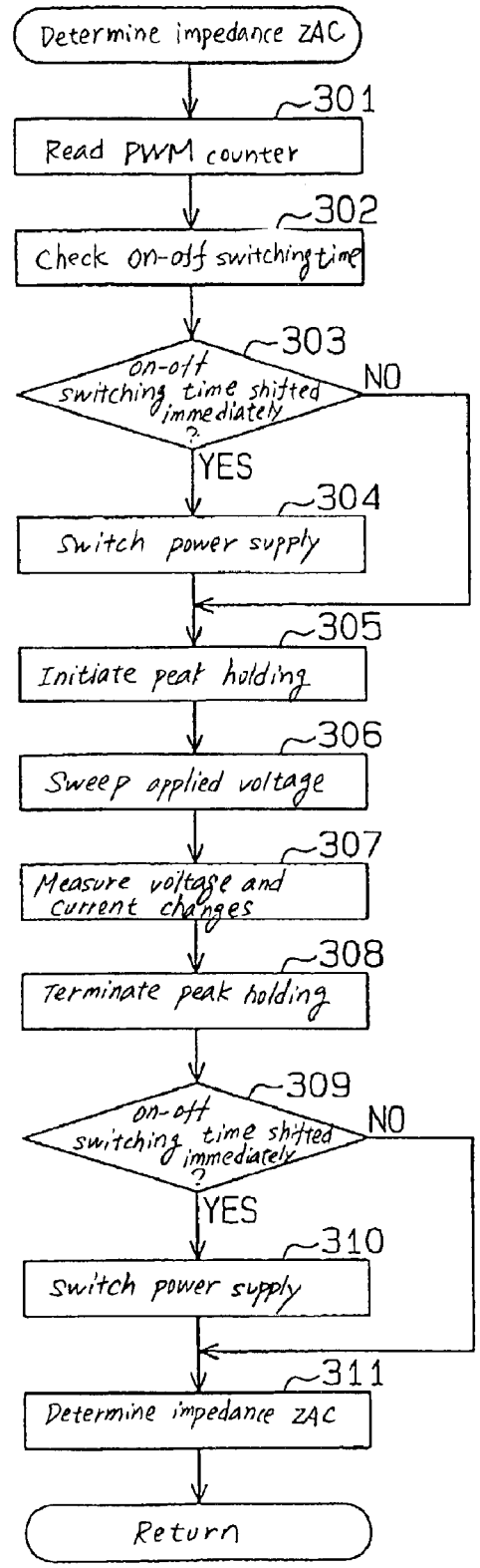
FIG. 16 is a flowchart of a program executed to determine the impedance of a sensor element in the second embodiment of the invention.

FIG. 16 shows a flowchart of a program performed by the control circuit 200 at a regular interval of 128 msec. to measure the sensor element impedance ZAC. This program corresponds to the one shown in FIG. 5. Specifically, the control circuit 200 executes the programs of FIGS. 4 and 6 and initiates the program of FIG. 16 in step 130 of the program of FIG. 4. The control circuit 200 also determines the concentration of NOx in the program of FIG. 4, but however, it is not essential part of this invention and explanation thereof in detail will be omitted here.

After entering the program of FIG. 16, the routine proceeds to step 301 wherein a count value is read out of the PWM counter. The routine proceeds to step 302 wherein a time at which the power supply to the heater 151 will be switched on or off is calculate or estimated based the count value read out in step 301 and the heater-on duration. Additionally, it is determined whether the estimated on-off switching time overlaps with the peak-holding time of the P/H circuit 220 or not. If an answer is positive, it is also determined whether the on-off switching time should be advanced or retarded outside the peak-holding time. One of these two alternatives is selected preferably which results in a smaller change in duty cycle DUTY of the heater power supply control signal, thereby minimizing an undesirable change in heater on-duration for which the power is supplied to the heater 151.

The routine proceeds to step 303 wherein it is determined whether the on-off switching should be shifted immediately or not. If it is estimated that the estimated on-off switching time will overlap with the peak-holding time of the P/H circuit 220, it is determined that the on-off switching time should be advanced, and it is determined that the advanced on-off switching time has been reached, a YES answer is obtained. The routine then proceeds to step 304 wherein the power supply to the heater 151 is switched on or off immediately.

The routine proceeds to step 305 wherein the P/H circuit 220 is activated to initiate monitoring of the peak of the voltage Vc applied to the monitor cell 120 (i.e., the peak of the voltage Ve). The routine proceeds to step 306 wherein the voltage Vc applied to the monitor cell 120 is swept or changed instantaneously. The routine proceeds to step 307 wherein a change in voltage Vc and a resulting change in monitor cell current Im are measured. The routine proceeds to step 308 wherein the P/H circuit 220 is deactivated to terminate the monitoring of the peak of the voltage Vc.

The routine proceeds to step 309 wherein it is determined whether the on-off switching should be shifted immediately or not. If it is estimated in step 302 that the estimated on-off switching time will overlap with the peak-holding time of the P/H circuit 220, it is determined that the on-off switching time should be retarded, and it is determined that the retarded on-off switching time has been reached, a YES answer is obtained. The routine then proceeds to step 310 wherein the power supply to the heater 151 is switched on or off immediately.

The routine proceeds to step 311 wherein the sensor element impedance ZAC is determined using the changes in voltage Vc and monitor cell current Im as measured in step 307.

The P/H circuit 200 may not be used. In the absence of the P/H circuit 200, the A/D converter is turned on only when the changes in voltage Vc and monitor cell current Im are measured. In this case, the on-off switching time at which the power supply to the heater 151 is to be switched on or off is shifted from the time the A/D converter is turned on.

Figure 17:
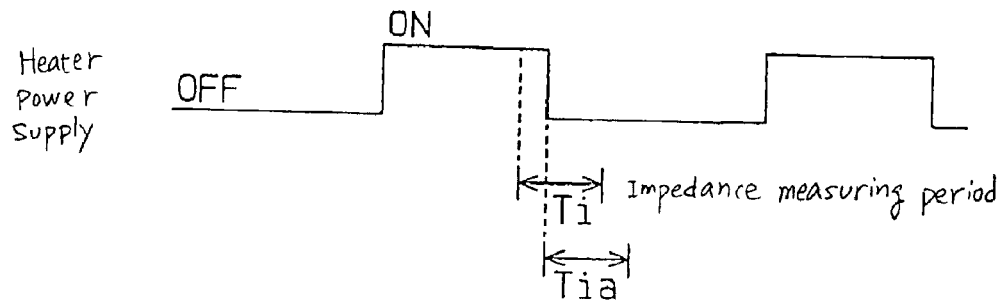
FIG. 17 shows a modification of measurement of a sensor element impedance.

FIG. 17 shows a modification of the measurement of the sensor element impedance ZAC which, instead of shifting of the on-off switching time of the power supply to the heater 151 as described above, defers the impedance measuring period Ti until completion of the on-off switching of the power supply to the heater 151 if it is determined that the on-off switching time will overlap with the impedance measuring period Ti.

In the illustrated case, the impedance measuring period is shifted from Ti to Tia. Other arrangements and operations are the same as described above, and explanation thereof in detail will be omitted.

Figure 18:
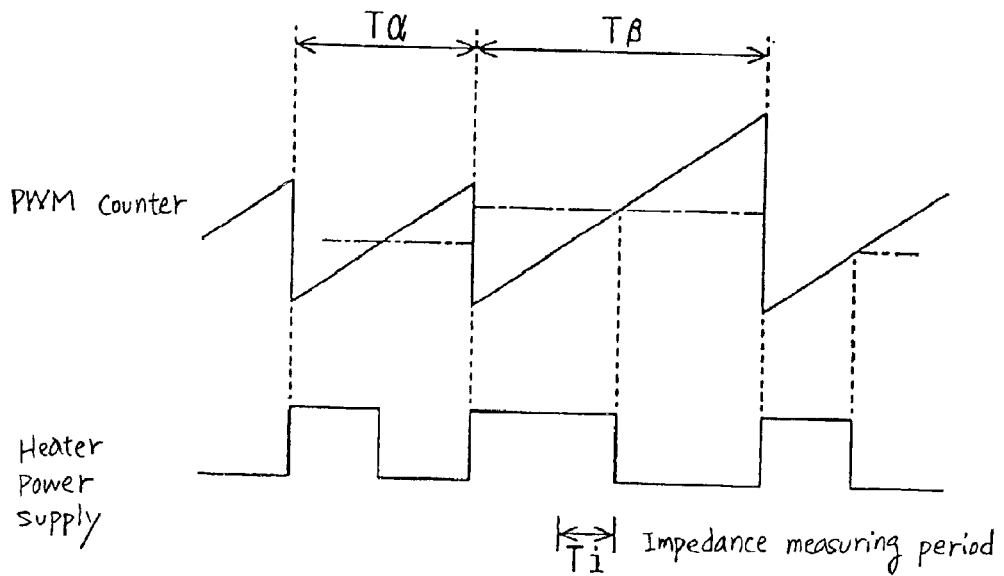
FIG. 18 shows the second modification of measurement of a sensor element impedance.

FIG. 18 the second modification of the measurement of the sensor element impedance ZAC which changes the cycle of the PWM of the power supply control signal for the heater 151 if it is determined that the on-off switching time will overlap with the impedance measuring period Ti.

In the illustrated case, the cycle of the PWM is extended from Tα to Tβ. If the cycle of the PWM matches up with the cycle of measurement of the impedance ZAC, that is, if the measurement of the impedance ZAC is n times or 1/n times the PWM in cycle, such extension may be performed only one time, after which the matching between the cycle of the PWM and the cycle of measurement of the impedance ZAC is established immediately.

Figure 19:
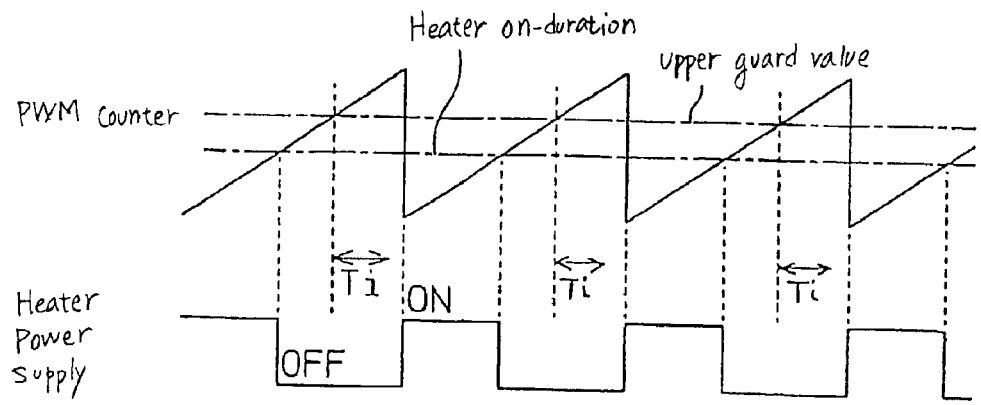
FIG. 19 shows the third modification of measurement of a sensor element impedance.

In the case where the cycle of the PWM matches up with or is synchronized with the cycle of measurement of the impedance ZAC, the third modification, as shown in FIG. 19, may also be used which defines an upper or a lower limit of the duty cycle DUTY of the power supply signal for the heater 151.

In the illustrated case, an upper guard value is provided to prevent the heater on-duration from exceeding it to cause the on-off switching time to overlap with the impedance measuring period Ti. Alternatively, if it is determined that the impedance measuring period Ti will appear immediately following the heater on-duration, a lower guard value for the heater on-duration may be provided.

The control circuit 200 of the air-fuel ratio measuring device 15 is designed to measure the impedance ZAC of the monitor cell 120 of the gas concentration sensor 100, but may instead measure the impedance of the pump cell 110 or the sensor cell 130. Alternatively, the impedance ZAC may be determined by the average of impedances of two or all of the pump cell 110, the monitor cell 120, and the sensor cell 130. The air-fuel ratio measuring device 15 may be used with a system in which a plurality of gas sensors are installed in the exhaust pipe of the engine. In this case the control circuit 200 are designed preferably to control the on-off switching of the power supply to the heaters of all the gas sensors so as not to overlap with the impedance measuring duration Ti independently.

The following modification may be used in this invention.

In a case where the duty cycle DUTY is limited using the upper or lower limit in step 150 or 151 of the program shown in FIG. 6, the accuracy of the correction of the duty cycle DUTY in step 149 may be lowered by extending a correction cycle in which the duty cycle DUTY is to be corrected. This results in a decrease in operation load of the microcomputer 20.

The heater voltage and the heater current may be allowed to be measured only when the on-time of the duty cycle DUTY is longer than a given value. For instance, such measurement is allowed only when the duty cycle DUTY is greater than or equal to 50%. This results in a decrease in operating load of the microcomputer 20 and alleviate the following problem. The heater voltage and the heater current is performed during energization of the heater 39 (151). If the on-time of the duty cycle DUTY is too short, it becomes difficult to measure the heater voltage and the heater current accurately.

The correction of the duty cycle DUTY may be made using a measurement history. For instance, the duty cycle DUTY is determined using the following equation.

$$DUTY = DUTY_{output} \times (DUTY_{now}/DUTY_{pre}) \times (V_{pre}/V_{now})$$

where $DUTY_{output}$ is the duty cycle of the power supply control signal outputted in a previous program execution cycle (e.g., one program cycle earlier), $DUTY_{now}$ is the duty cycle calculated in a current program execution cycle, $DUTY_{pre}$ is the duty cycle calculated in the previous program execution cycle, $V_{pre}$ is the heater voltage measured in the previous program execution cycle, and $V_{now}$ is the heater voltage measured in the current program cycle.

The above correction of the duty cycle DUTY also result in improved controllability of the power supply to the heater 39 (151).

The term $(V_{pre}/V_{now})$ may alternatively be replaced with $(V_{pre}^2/V_{now}^2)$, $(A_{pre}/A_{now})$, or $(A_{pre}^2/A_{now}^2)$ where A is a measured current flowing through the heater 39 (151). The use of $(V_{pre}^2/V_{now}^2)$ or $(A_{pre}^2/A_{now}^2)$ results in increased accuracy of the correction of the duty cycle DUTY.

The power supply control, as discussed in FIG. 6, guards the duty cycle DUTY from an undesirable change using the upper and lower limits (i.e., the upper and lower guard values), but however, both or either of these limits may be omitted. It is also advisable that both the upper and lower limits be increased, that is, a range between the upper and lower limits be shifted to a greater percentage side with an increase in sensor element impedance ZAC for avoiding the premature activation of the sensor element subjected to a lower temperature and damage of the sensor element subjected to a high temperature.

Instead of the sensor element impedance ZAC, the admittance that is the reciprocal of the impedance ZAC may be used. Additionally, switching between the impedance ZAC and the admittance may be performed as a function of the temperature of the sensor element (i.e., the measure of activation of the sensor element).

The air-fuel ratio control device 15, as described above, has the A/F sensor 30 or the gas concentration sensor 100 installed in the exhaust pipe of the engine 10 to measure an oxygen content in exhaust gasses, but may install a similar sensor in an induction pipe of the engine 10 instead of or in addition to the A/F sensor 30 or the gas concentration sensor 100 to measure an oxygen content in induction gasses for use in controlling the air-fuel ratio of mixture. In this case, an output of the sensor installed in the induction pipe may be used to control an exhaust gas recirculation (EGR) system.

The output of the sensor installed in the induction pipe of the engine may also be employed in an evaporative emission control system. Specifically, the concentration of fuel vapors which are evaporated within a fuel tank, accumulated in a canister, and then discharged into the induction pipe of the engine is measured by the sensor to correct the quantity of fuel injected into the engine.

The present invention is used with the air-fuel ratio control device 15 equipped with the A/F sensor 30 or the gas concentration sensor 100 designed to measure an oxygen content in the exhaust gasses, but may alternatively be used with air-fuel ratio control systems equipped with another type of gas sensor which measures nitrogen oxide (NOx), hydro carbon (HC), and/or carbon monoxide (CO).

What is claimed is:

1. A heater control apparatus comprising:
   a control circuit working to control a power supply to a heater used to heat a solid electrolyte-made sensor element of a gas concentration sensor up to a temperature at which the sensor element is activated to provide a desired gas concentration output;
   a sensor element resistance determining circuit working to determine a resistance value of the sensor element of the gas concentration sensor;
   a heater control variable determining circuit determining a heater control variable for controlling the power supply to the heater in said control circuit as a function of a difference between the resistance value determined by said sensor element resistance determining circuit and a target value; and
   a heater control variable correcting circuit correcting the heater control variable determined by said heater control variable determining circuit based on a comparison between a given reference heater power and a heater power actually used in the heater.

2. A heater control apparatus as set forth in claim 1, wherein said heater control variable correcting circuit corrects the heater control variable based on a comparison between a voltage appearing at the heater and a reference voltage preselected for the heater.

3. A heater control apparatus as set forth in claim 1, wherein said heater control variable correcting circuit corrects the heater control variable based on a comparison between a current flowing through the heater and a reference current preselected for the heater.

4. A heater control apparatus as set forth in claim 1, further comprising a guard value providing means for providing a guard value working to defines a limit of the heater control variable, the guard value being increased with an increase in the resistance value of said sensor element determined by said sensor element resistance determining circuit.

5. A heater control apparatus as set forth in claim 1, wherein said control circuit works to supply power to the heater in a cycle and controls an on-time for which the power is supplied to the heater, said control circuit allows said heater control variable correcting circuit to determine one of a heater voltage developed at the heater and a current flowing through the heater which is employed to determine the heater power consumed in the heater only when the on-time is longer than a given reference value.

6. A heater control apparatus as set forth in claim 1, wherein said control circuit is responsive to the heater control variable to switch the power supply to the heater on and off cyclically, and wherein said sensor element resistance determining circuit measures the resistance value of the sensor element in a cycle by changing one of a voltage applied to the heater and a current flowing through the heater instantaneously, monitoring a change in the one of the voltage and the current, and calculating the resistance value as a function of the change, when it is determined that an on-off switching time at which the power supply to the heater is to be switched on or off will overlap with a measurement time for which the resistance value is to be measured, said sensor element resistance determining circuit shifting one of the on-off switching time and the measurement time.

7. A heater control apparatus comprising:
   a control circuit controlling a power supply to a heater used to heat a solid electrolyte-made sensor element of a gas concentration sensor up to a temperature at which the sensor element is activated to provide a desired gas concentration output;
   a sensor element resistance determining circuit working to determine a resistance value of the sensor element of the gas concentration sensor;
   a heater control variable determining circuit determining a heater control variable which is used in said control circuit in controlling the power supply to the heater as a function of a difference between the resistance value determined by said sensor element resistance determining circuit and a target value; and
   a heater control variable correcting circuit determining one of a heater voltage developed at the heater and a heater current flowing through the heater in a cycle, said heater control variable correcting circuit correcting the heater control variable determined by said heater control variable determining circuit based on a comparison between one of the heater voltage and the heater current as determined in a current cycle and a corresponding one of the heater voltage and the heater current as determined in a previous cycle.

8. A heater control apparatus as set forth in claim 7, further comprising a guard value providing means for providing a guard value working to define a limit of the heater control variable, the guard value being increased with an increase in the resistance value of said sensor element determined by said sensor element resistance determining circuit.

9. A heater control apparatus as set forth in claim 8, wherein said control circuit provides a power supply control signal to a heater driver to bring the resistance value into agreement with the target value under feedback control for controlling the power supply to the heater, the power supply control signal being provided using a mathematical formula including an integral term in terms of the difference between the resistance value determined by said sensor element resistance determining circuit and the target value, further comprising a decision means for deciding whether the resistance value as determined by said sensor element resistance determining circuit falls within a given controlled range or not, and wherein when it is determined by said decision means that the resistance value lies out of the given range, said guard value providing means determines the guard value so as to decrease a change in the resistance value from the target value.

10. A heater control apparatus as set forth in claim 9, wherein said guard value providing means defines a first guard value and a second guard value, the first guard value being provided to determine a maximum value of the heater control variable when said decision means determines that the resistance value lies out of said given controlled range to a side on which a temperature of the sensor element is higher, the second guard value being provided to determine a minimum value of the heater control variable when said decision means that the resistance value lies out of the given controlled range to a side on which the temperature of the sensor element is lower.

11. A heater control apparatus as set forth in claim 9, wherein said control circuit works to supply power to the heater in a cycle and controls an on-time for which the power is supplied to the heater, said control circuit allows said heater control variable correcting circuit to determine one of a heater voltage developed at the heater and a current flowing through the heater which is employed to determine the heater power consumed in the heater only when the on-time is longer than a given reference value.

12. A heater control apparatus as set forth in claim 7, wherein said control circuit is responsive to the heater control variable to switch the power supply to the heater on and off cyclically, and wherein said sensor element resistance determining circuit measures the resistance value of the sensor element in a cycle by changing one of a voltage applied to the heater and a current flowing through the heater instantaneously, monitoring a change in the one of the voltage and the current, and calculating the resistance value as a function of the change, when it is determined that an on-off switching time at which the power supply to the heater is to be switched on or off will overlap with a measurement time for which the resistance value is to be measured, one of the on-off switching time and the measurement time being shifted.

13. A gas concentration sensor control apparatus comprising:
a gas concentration sensor having a solid electrolyte-made sensor element producing a sensor output indicative of a concentration of a specified gas component:
a heater installed in said gas concentration sensor to heat the sensor element up to a temperature at which the sensor element is activated to produce the sensor output correctly;
a heater power supply control circuit working to turn on and off a power supply to said heater cyclically;
a sensor element resistance determining circuit working to measure a resistance value of the sensor element in a cycle by changing one of a voltage applied to said heater and a current flowing through said heater instantaneously, monitoring a change in the one of the voltage and the current, and calculating the resistance value as a function of the change;
a heater control variable determining circuit determining a heater control variable, which is used in said heater power supply control circuit to define an on-time for which the power supply to said heater is to be turned on and an off-time for which the power supply to said heater is to be turned off, as a function of a difference between the resistance value determined by said sensor element resistance determining circuit and a target value; and
a control circuit determining whether an on-off switching time at which the power supply to said heater is to be switched on or off will overlap with a measurement time for which the resistance value is to be measured, when it is determined that the on-off switching time will overlap with the measurement time, said control circuit shifting one of the on-off switching time and the measurement time.

14. A gas concentration sensor control apparatus as set forth in claim 13, wherein when it is determined that the on-off switching time will overlap with the measurement time, said control circuit brings the on-off switching time outside the measurement time.

15. A gas concentration sensor control apparatus as set forth in claim 14, wherein when it is determined that the on-off switching time will overlap with the measurement time, said control circuit brings the on-off switching time outside one of start and end of the measurement time which results in a smaller change in either of the on-time and the off-time.

16. A gas concentration sensor control apparatus as set forth in claim 13, wherein when it is determined that the on-off switching time will overlap with the measurement time, said control circuit delays measurement of the resistance value until completion of on-off switching of the power supply to said heater.

17. A gas concentration sensor control apparatus as set forth in claim 13, wherein the heater control variable is a duty cycle of a power supply control signal that is a ratio of the on-time to the off-time, and wherein when it is determined that the on-off switching time will overlap with the measurement time, said control circuit increases or decreases the duty cycle.

18. A gas concentration sensor control apparatus as set forth in claim 13, wherein the heater control variable is a duty cycle of a power supply control signal that is a ratio of the on-time to the off-time, wherein the duty cycle is synchronized with the measurement time, and wherein an upper or a lower value of the duty cycle is determined to prevent the on-off switching time from overlapping with the measurement time.

19. A gas concentration sensor control apparatus as set forth in claim 13, wherein said gas concentration sensor has a plurality of cells disposed on a solid electrolyte body of the sensor element, said sensor element resistance determining circuit measuring respective resistance values of the cells to determine the resistance value of the sensor element, and wherein said control circuit shifts one of the on-off switching time and each measurement time for which one of the resistance values is measured so that the on-off switching time lies out of each measurement time.

20. A gas concentration sensor control apparatus as set forth in claim 13, further comprising a second gas concentration sensor having a solid electrolyte-made sensor element producing a sensor output indicative of a concentration of a specified gas component and a second heater installed in said second gas concentration sensor to heat the sensor element up to a temperature at which the sensor element is activated to produce the sensor output correctly, and wherein said heater power supply control circuit works to turn on and off a power supply to said second heater cyclically, said sensor element resistance determining circuit works to measure a resistance value of the sensor element of said second gas concentration sensor in a cycle by changing one of a voltage applied to said second heater and a current flowing through said second heater instantaneously, monitoring a change in the one of the voltage and the current, and calculating the resistance value of said second gas concentration sensor as a function of the change, said heater control variable determining circuit determines a heater control variable, which is used in said heater power supply control circuit to define an on-time for which the power supply to said second heater is to be turned on and an off-time for which the power supply to said second heater is to be turned off, as a function of a difference between the resistance value of said second gas concentration sensor and a target value, and said control circuit determines whether an on-off switching time at which the power supply to said second heater is to be switched on or off will overlap with a measurement time for which the resistance value of said second gas concentration sensor is to be measured, when it is determined that the on-off switching time will overlap with the measurement time, said control circuit shifting one of the on-off switching time and the measurement time.

21. A gas concentration sensor control apparatus as set forth in claim 13, further comprising a peak hold circuit working to hold a peak of the change in the one of the voltage and the current for use in calculating the resistance value, and wherein the measurement time is a time for which the peak is held by the peak hold circuit.

22. A gas concentration sensor control apparatus as set forth in claim 13, said sensor element resistance determining circuit picks up the change in the one of the voltage and the current through an A/D converter, and wherein the measurement time contains a time for which the change is picked up through the A/D converter.

* * * * *